United States Patent
King et al.

(10) Patent No.: US 11,752,343 B2
(45) Date of Patent: Sep. 12, 2023

(54) PERIPHERAL NERVE FIELD STIMULATION CONTROL

(71) Applicant: Medtronic, Inc., Minneapolis, MN (US)

(72) Inventors: Gary W. King, Fridley, MN (US); Steven M. Goetz, North Oaks, MN (US); Andrew H. Houchins, Hugo, MN (US); Jeffrey T. Keacher, Stanford, CA (US); Jordan J. Greenberg, Blaine, MN (US); Kenneth T. Heruth, Edina, MN (US); Mark S. Lent, Brooklyn Park, MN (US); Paul W. Wacnik, Brookline, MA (US)

(73) Assignee: Medtronic, Inc., Minneapolis, MN (US)

( * ) Notice: Subject to any disclaimer, the term of this patent is extended or adjusted under 35 U.S.C. 154(b) by 308 days.

(21) Appl. No.: 16/985,955

(22) Filed: Aug. 5, 2020

(65) Prior Publication Data

US 2020/0368532 A1  Nov. 26, 2020

Related U.S. Application Data

(60) Division of application No. 14/454,427, filed on Aug. 7, 2014, now Pat. No. 10,744,326, which is a (Continued)

(51) Int. Cl.
*A61N 1/36* (2006.01)

(52) U.S. Cl.
CPC ..... *A61N 1/36139* (2013.01); *A61N 1/36057* (2013.01); *A61N 1/36071* (2013.01)

(58) Field of Classification Search
CPC ............ A61N 1/36057; A61N 1/36071; A61N 1/36139
See application file for complete search history.

(56) References Cited

U.S. PATENT DOCUMENTS

| 4,595,010 A | 6/1986 | Radke |
| 5,702,429 A | 12/1997 | King |

(Continued)

OTHER PUBLICATIONS

Communication pursuant to Article 94(3) EPC from corresponding European Patent Application No. 09743106.8, dated Sep. 20, 2013, 4 pp.

(Continued)

*Primary Examiner* — Alyssa M Alter
(74) *Attorney, Agent, or Firm* — Shumaker & Sieffert, P.A.

(57) ABSTRACT

Peripheral nerve field stimulation (PNFS) may be controlled based on detected physiological effects of the PNFS, which may be an efferent response to the PNFS. In some examples, a closed-loop therapy system may include a sensing module that senses a physiological parameter of the patient, which may be indicative of the patient's response to the PNFS. Based on a signal generated by the sensing module, the PNFS may be activated, deactivated or modified. Example physiological parameters of the patient include heart rate, respiratory rate, electrodermal activity, muscle activity, blood flow rate, sweat gland activity, pilomotor reflex, or thermal activity of the patient's body. In some examples, a patient pain state may be detected based on a signal generated by the sensing module, and therapy may be controlled based on the detection of the pain state.

19 Claims, 19 Drawing Sheets

Related U.S. Application Data continuation of application No. 12/359,001, filed on Jan. 23, 2009, now Pat. No. 8,805,518.

(60) Provisional application No. 61/051,955, filed on May 9, 2008.

(56) References Cited

U.S. PATENT DOCUMENTS

| | | | |
|---|---|---|---|
| 6,058,331 | A | 5/2000 | King |
| 6,609,032 | B1 | 8/2003 | Woods et al. |
| 6,733,485 | B1 | 5/2004 | Whitehurst et al. |
| 6,845,267 | B2 | 1/2005 | Harrison et al. |
| 6,909,917 | B2 | 6/2005 | Woods et al. |
| 7,123,967 | B2 | 10/2006 | Weinberg |
| 7,184,837 | B2 | 2/2007 | Goetz |
| 7,218,964 | B2 | 5/2007 | Hill et al. |
| 7,239,926 | B2 | 7/2007 | Goetz |
| 7,305,268 | B2 | 12/2007 | Gliner et al. |
| 7,813,803 | B2 | 10/2010 | Heruth et al. |
| 8,805,518 | B2 | 8/2014 | King et al. |
| 10,744,326 | B2 | 8/2020 | King et al. |
| 2004/0138517 | A1 | 7/2004 | Osorio et al. |
| 2005/0021104 | A1 | 1/2005 | DiLorenzo |
| 2005/0043774 | A1 | 2/2005 | Devlin et al. |
| 2005/0070969 | A1 | 3/2005 | Gerber |
| 2005/0143789 | A1 | 6/2005 | Whitehurst et al. |
| 2006/0155333 | A1 | 7/2006 | Goetz |
| 2006/0206165 | A1 | 9/2006 | Jaax et al. |
| 2006/0229687 | A1 | 10/2006 | Goetz et al. |
| 2007/0021801 | A1 | 1/2007 | Heruth et al. |
| 2007/0032834 | A1 | 2/2007 | Gliner et al. |
| 2007/0073353 | A1 | 3/2007 | Rooney et al. |
| 2007/0073356 | A1 | 3/2007 | Rooney et al. |
| 2007/0213783 | A1 | 9/2007 | Pless |
| 2007/0255346 | A1 | 11/2007 | Rondoni et al. |
| 2007/0255351 | A1 | 11/2007 | Begnaud et al. |
| 2007/0265664 | A1 | 11/2007 | Gerber et al. |
| 2007/0265681 | A1* | 11/2007 | Gerber ............... A61N 1/36071 607/46 |
| 2008/0051839 | A1 | 2/2008 | Libbus et al. |
| 2008/0071324 | A1* | 3/2008 | Miesel ................. A61B 5/4815 607/46 |

OTHER PUBLICATIONS

Examination Report from Counterpart European Patent Application No. 09743106.8, dated Sep. 3, 2014, 4 pp.
International Search Report and Written Opinion dated Oct. 7, 2009 for corresponding PCT Application No. PCT/US2009/031852, 17 pp.
Invitation to Pay Additional Fees and, Where Applicable, Protest Fee dated May 15, 2009 for corresponding PCT Application No. PCT/US2009/031852, 6 pp.
Notification Concerning Transmittal of International Preliminary Report on Patentability, dated Nov. 18, 2010 for corresponding PCT/US2009/031852, 11 pp.
Prosecution History from U.S. Appl. No. 12/359,001, dated Jul. 8, 2011 through Apr. 9, 2014, 85 pp.
Response to counterpart European Application No. 09743106.8 Office Action dated Sep. 3, 2014, filed on Jan. 9, 2015, 6 pp.
Response to European office action dated Sep. 20, 2013 for counterpart European patent application No. 09743106.8, filed Dec. 20, 2013, 5 pp.
Prosecution History from U.S. Appl. No. 14/454,427, dated Jun. 16, 2016 through Apr. 9, 2020, 196 pp.
Preliminary Amendment from counterpart European Application No. 09743106.8, dated Dec. 8, 2010, 10 pp.
Response to Communication Pursuant to Rule 161(1) EPC dated Mar. 10, 2011, from counterpart European Application No. 09743106.8, filed Apr. 19, 2011, 8pp.
Summons to Attend Oral Proceedings Pursuant to Rule 115(1) EPC from counterpart European Application No. 19743106.8, dated May 8, 2015, 5 pp.
Notice of Intent to Grant and Text Intended to Grant from counterpart European Application No. 09743106.8, dated Apr. 7, 2016, 87 pp.
Decision to Grant from counterpart European Application No. 09743106.8, dated Aug. 19, 2016, 2 pp.

* cited by examiner

PERIPHERAL NERVE FIELD STIMULATION CONTROL

This application is a divisional of U.S. patent application Ser. No. 14/454,427, filed Aug. 7, 2014, which is a continuation of U.S. patent application Ser. No. 12/359,001, filed on Jan. 23, 2009, now U.S. Pat. No. 8,805,518, which claims the benefit of U.S. Provisional Patent Application No. 61/051,955, filed on May 9, 2008. The entire contents of U.S. Provisional Patent Application No. 61/051,955, U.S. patent application Ser. No. 12/359,001, and U.S. patent application Ser. No. 14/454,427 are incorporated herein by reference.

TECHNICAL FIELD

The disclosure relates to medical devices, and, more particularly, to control of therapy delivery by medical devices.

BACKGROUND

A variety of therapies, such as neurostimulation or therapeutic agents, e.g., drugs, may be delivered to a patient to treat chronic or episodic pain. Examples of neurostimulation therapies used to treat pain are transcutaneous electrical nerve stimulation (TENS), percutaneous electrical nerve stimulation (PENS), peripheral nerve stimulation (PNS), spinal cord stimulation (SCS), deep brain stimulation (DBS), and cortical stimulation (CS). Examples of drugs used to treat pain are opioids, cannabinoids, local anesthetics, baclofen, adenosine and alpha-blockers.

PNS, SCS, DBS and CS are typically delivered by an implantable medical device (IMD). An IMD delivers electrical stimulation therapy via electrodes, which are typically coupled to the IMD by one or more leads. The number and positions of the leads and electrodes is largely dependent on the type or cause of the pain, and the type of neurostimulation delivered to treat the pain. In general, an IMD delivers neurostimulation therapy in the form of electrical pulses.

SCS involves stimulating the spinal cord at specifically targeted locations, typically via leads and electrodes that are either surgically implanted post laminectomy, or inserted percutaneously in the epidural space. Delivering stimulation to the appropriate location on the spinal cord causes paresthesia that overlays the pain region to reduce perception of pain. SCS can result in the patient experiencing paresthesia in a relatively large area, including more than one limb. In some cases, SCS may be effective for neuropathic pain, such as neuropathy or radiculopathy that involves a significant portion of one limb and more than one dermatome.

PNS is typically used to treat patients suffering from intractable pain associated with a single nerve. PNS places a group of electrodes in very close proximity to, e.g., in contact with, and approximately parallel to a major nerve in the subcutaneous tissue. PNS may also place a group of electrodes in very close proximity to a nerve that may be deeper in the limb. Placing electrodes in very close proximity to the nerve may ensure that only fibers within that nerve are activated at low amplitudes.

PNS electrodes may be located on percutaneous leads, but for stability and to prevent stimulation of other tissues proximate to the target peripheral nerve, PNS electrodes are generally located within insulative material that wraps around a nerve, e.g., cuff electrodes, or on one surface of a flat paddle of insulative material placed under a nerve. In any case, the electrodes for PNS are placed in close proximity to the nerve "upstream" from the source of damage or pain, e.g., closer to the spinal cord than the region of damage or pain. When electrodes are implanted upstream, the paresthesia resulting from PNS may extend to a broader area innervated by the target peripheral nerve. Examples of upper extremity nerves that may be treated with PNS include the ulnar nerve, median nerve, radial nerve, tibial nerve and common peroneal nerve.

DBS and CS can be used to treat neuropathic and nociceptive pain through delivery of stimulation to various structures of the brain. In some cases, DBS may treat pain through delivery of stimulation to gray matter within the midbrain, or the thalamus, via electrodes implanted in the brain. CS may treat pain through delivery of stimulation to the sensory and/or motor cortex via electrodes placed in or on the cortex.

Therapeutic agents that treat pain may be delivered by an implantable pump, external pump, transdermally, or orally. Typically, an implantable pump delivers one or more therapeutic agents to a target location via a catheter. The target location may be intrathecal or extradural.

SUMMARY

In general, the disclosure describes techniques for controlling stimulation therapy, such as peripheral nerve field stimulation (PNFS), based on detected physiological effects of the therapy on a patient. In some examples, a desired physiological effect of PNFS may be associated with a particular physiological parameter of the patient, and therapy may be delivered to the patient based on the detection of a physiological parameter characteristic. Example physiological parameters of the patient include heart rate, respiratory rate, electrodermal activity (e.g., galvanic skin response or skin conductance response), muscle activity (e.g., electromyogram (EMG)), blood flow rate, sweat gland activity, pilomotor reflex (e.g., goose bumps), or thermal activity of the patient's body. The physiological parameter characteristic may be, for example, an amplitude, trend, or frequency band characteristic of a signal that changes as a function of the physiological parameter (e.g., a "physiological signal"). In other examples, the desired physiological parameter characteristic may be a characteristic of a physiological signal from a control physiological signal. The control physiological signal may indicate the activity of the physiological parameter within a region of the patient's body that is generally unaffected by the delivery of PNFS. For example, the control signal may be indicative of the physiological parameter in a portion of the patient's body outside of the region in which the PNFS is delivered, which may also be the region in which the patient perceives pain.

In one technique for controlling therapy delivery, therapy may be delivered until the physiological parameter characteristic is detected. In another example technique, therapy may be delivered to maintain the physiological parameter characteristic above a threshold, within a certain window of values, or below a threshold.

In some examples, PNFS is delivered to the patient to generate an afferent response, such as to relieve pain. The stimulation therapy may incidentally activate efferent nerves, thereby resulting in an efferent response from the patient, which may generate a detectable change in a physiological parameter of the patient. The detected physiological effects of the therapy on the patient that is used to control therapy may, therefore, be an efferent response. In this way, the patient's efferent response to stimulation may be used in a closed-loop therapy system in order to control the therapy delivery, such as to activate or deactivate therapy delivery or to titrate the therapy parameter values.

In some examples, a characteristic of a physiological signal may be associated with a patient pain state. The physiological signal may be indicative of a patient parameter that changes in response to delivery of PNFS therapy. Detection of the pain state via the characteristic of the physiological signal may be used in a closed-loop therapy system to control the delivery of PNFS to the patient. In some examples, a device monitors a physiological signal of a patient and determines whether the signal indicates the patient is in a pain state. The device may control the delivery of PNFS to a patient based on the detection of the pain state.

In one example, the disclosure describes a method comprising delivering peripheral nerve field stimulation to a region of a body of a patient in which the patient experiences pain via at least one electrode implanted in the region, receiving a signal indicative of a physiological parameter of the patient, wherein the signal indicates a response of the patient to the peripheral nerve field stimulation, and controlling the delivery of the peripheral nerve field stimulation based on the signal.

In another example, the disclosure describes a method comprising delivering peripheral nerve field stimulation to a region of a body of a patient in which the patient experiences pain via at least one electrode implanted in the region, detecting an efferent response of the patient to the delivery of peripheral nerve field stimulation, and controlling the delivery of the peripheral nerve field stimulation based on the detected efferent response.

In another example, the disclosure describes a system comprising a sensing module that generates a signal indicative of a physiological parameter of a patient, a medical device that delivers peripheral nerve field stimulation to a region of a body of the patient in which the patient experiences pain via at least one electrode implanted in the region, and a processor that receives the signal from the sensing module and controls the delivery of the peripheral nerve field stimulation by the medical device based on the signal. The signal indicates a response of the patient to the peripheral nerve field stimulation.

In another example, the disclosure describes a system comprising means for delivering peripheral nerve field stimulation to a region of a body of a patient in which the patient experiences pain via at least one electrode implanted in the region, means for receiving a signal indicative of a physiological parameter of the patient, wherein the signal indicates a response of the patient to the peripheral nerve field stimulation, and means for controlling the delivery of the peripheral nerve field stimulation based on the physiological signal.

In another example, the disclosure describes a method comprising receiving a signal indicative of a physiological parameter of a patient, determining a patient pain state based on the signal, and based on the patient pain state, controlling the delivery of peripheral nerve field stimulation to a region of a body of the patient in which the patient experiences pain via at least one electrode implanted in the region.

In another example, the disclosure describes a system comprising a sensing module that generates a signal indicative of a physiological parameter of a patient, a medical device that delivers peripheral nerve field stimulation to a region of a body of the patient in which the patient experiences pain via at least one electrode implanted in the region, and a processor that receives the signal from the sensing module, determines a patient pain state based on the signal, and controls the delivery of the peripheral nerve field stimulation based on the determined pain state.

In another example, the disclosure describes a system comprising means for receiving a signal indicative of a physiological parameter of a patient, means for determining a patient pain state based on the signal, and means for controlling delivery of peripheral nerve field stimulation to a region of a body of the patient in which the patient experiences pain based on the patient pain state. The peripheral nerve field stimulation is delivered via at least one electrode implanted in the region.

In another example, the disclosure describes a computer-readable medium containing instructions. The instructions cause a programmable processor to perform any of the techniques described herein.

DETAILED DESCRIPTION

Peripheral nerve field stimulation (PNFS) is electrical stimulation delivered via one or more implanted electrodes. The electrodes are positioned, i.e., implanted, in the tissue of a patient within the region in which the patient experiences pain. The electrodes may be implanted within, for example, intra-dermal, deep dermal, or subcutaneous tissues of the patient. The PNFS current may spread along paths of lower resistance in any of numerous directions from electrodes, but generally spreads parallel to the skin surface. The PNFS current may spread over an area of several square centimeters. PNFS is not deliberately delivered to a specific nerve, but may excite nearby nerves.

Depending on the location at which the electrodes are implanted, PNFS may be used to treat a variety of types of pain. PNFS may be particularly effective at treating localized types of pain. For example, PNFS may be used to treat pain associated with failed back surgery syndrome (FBBS) or other low back pain, cervical pain, such as in the shoulder or neck, neuralgia or other pain associated with occipital nerves, supra-orbital pain, facial pain, inguinal or other pelvic pain, intercostal or other chest pain, limb pains, phantom limb pain, visceral pain, especially if it is referred to a superficial structure, peroneal pain, or arthritis.

Figure 1:
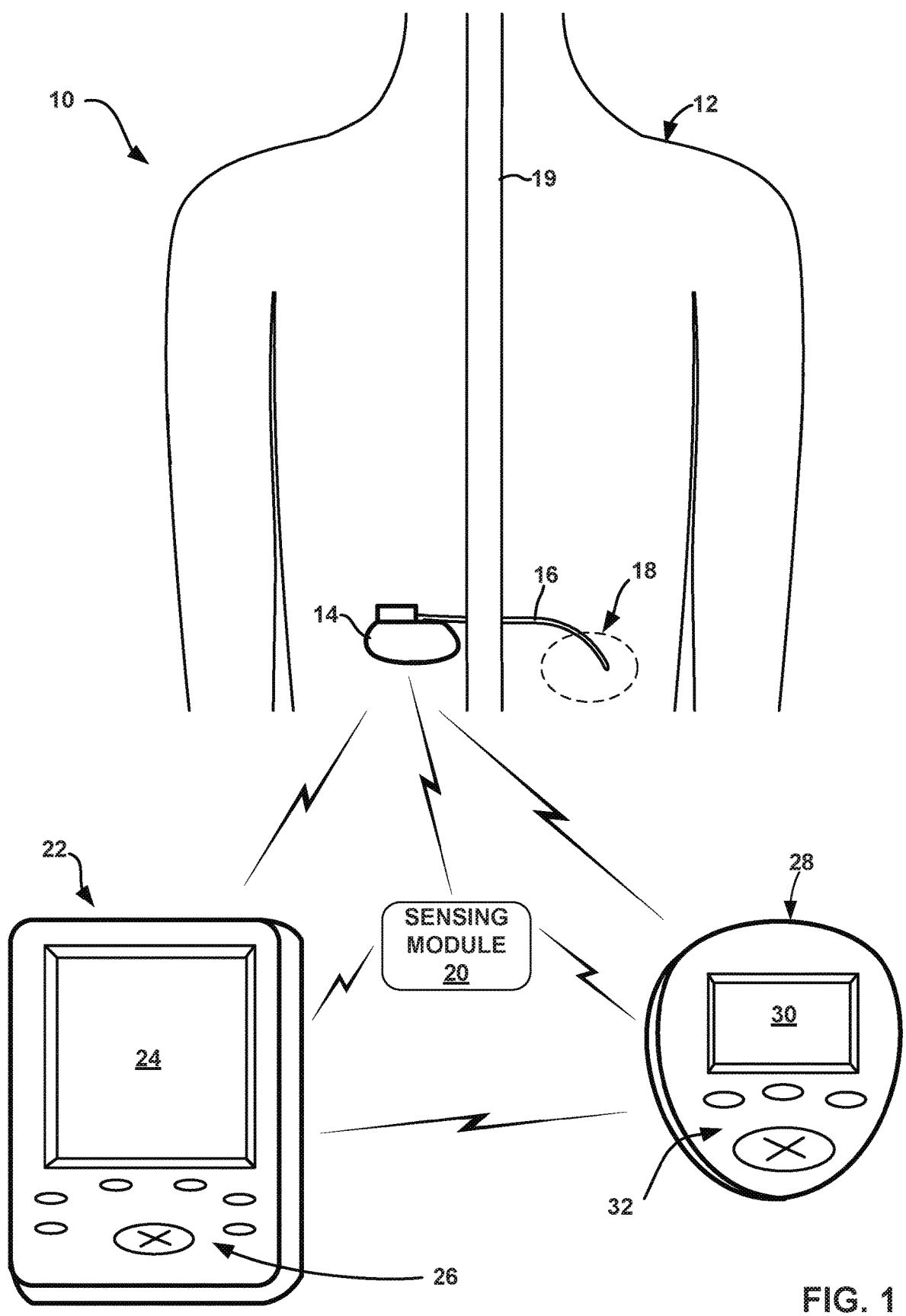
FIG. 1 is a conceptual diagram illustrating an example system for delivering peripheral nerve field stimulation (PNFS) to a patient.

FIG. 1 is a conceptual diagram illustrating an example therapy system 10 for treating pain of a patient 12 by delivering PNFS to patient 12. System 10 includes an implantable medical device (IMD) 14 that delivers PNFS therapy to patient 12. IMD 14 may include circuitry for the generation of electrical stimulation signals, which may be pulses as primarily described herein, or continuous time signals, such as sine waves, for delivery to patient 12 via selected combinations of electrodes (not shown in FIG. 1) carried by lead 16.

Lead 16 may comprise, for example, a substantially cylindrical lead with ring electrodes, a paddle lead, or a lead within a more complex, three-dimensional electrode array geometry, such as a cylindrical lead with electrodes disposed at various circumferential positions around the cylinder. In some examples, as discussed in greater detail below, the lead may have electrodes, such as pad electrodes, on more than one surface. For example, lead 16 may be a paddle-type lead with electrodes on multiple surfaces, or a multiple level lead, as described in commonly-assigned U.S. patent application Ser. No. 11/450,133 to Rooney et al., entitled, "COMBINATION THERAPY INCLUDING PERIPHERAL NERVE FIELD STIMULATION" and filed on Jun. 9, 2006. U.S. patent application Ser. No. 11/450,133 to Rooney et al. is incorporated herein by reference in its entirety. The devices, systems, and techniques described herein are not limited to use of any of the leads described herein, or any particular type of implantable lead.

In addition, in other examples, more than one lead may be coupled to IMD 14 to deliver PNFS to patient 12. For example, multiple leads may extend from IMD 14 to the same region or different regions of pain within patient 12. As an example, each of four leads 16, each with two electrodes, may extend to a respective, particular region 18 where patient 12 experiences pain. Lead 16 may be bifurcated, particularly if the number of interfaces that IMD 14 provides for electrically coupling a stimulation generator within IMD 14 to leads is limited. Although not shown in FIG. 1, lead 16 may be coupled to IMD 14 by one or more extensions. In some examples, IMD 14 may also include additional leads so as to deliver one or more other therapies, such as SCS, in combination with PNFS, e.g., as described in U.S. patent application Ser. No. 11/450,133 to Rooney et al.

Lead 16 delivers PNFS from IMD 14 to the tissue of patient 12 within a region 18 where patient 12 experiences pain. Lead 16 may be implanted within or between, for example, intra-dermal, deep dermal, or subcutaneous tissue of patient 12 at the region 18 where patient 12 experiences pain to deliver PNFS. Subcutaneous tissue includes skin and associated nerves, and muscles and associated nerves or muscle fibers. In the illustrated example, region 18 is an axial region of the lower back of patient 12. In other examples, lead 16 may be implanted in any region where patient 12 experiences pain. Lead 16 may deliver PNFS to one layer of tissue or multiple layers of a tissue as determined necessary by a physician.

In general, lead 16 may extend from IMD 14 to any localized area or dermatome in which patient 12 experiences pain. For example, lead 16 may extend from IMD 14 to position electrodes at various regions of the back, the back of the head, above the eyebrow, and either over the eye or under the eye, and may be used to treat failed back surgery syndrome (FBBS), cervical pain (e.g., shoulder and neck pain), facial pain, headaches supra-orbital pain, inguinal and pelvic pain, chest and intercostal pain, mixed pain (e.g., nociceptive and neuropathic), visceral pain, neuralgia, peroneal pain, phantom limb pain, and arthritis. Therapy system 10 is useful for managing pain associated with other patient conditions.

PNFS provided by therapy system 10 may ameliorate pain within the region of implantation by stimulating axons or small nerve fibers in the nearby dermal, subcutaneous, or muscular tissues, or the tissues themselves. The stimulation of these axons or fibers may cause orthodromic action potentials that propagate toward spinal cord 19, and modulate larger peripheral nerves and dorsal horn cells and/or synapses within the dermatomes that include the pain region, which may reduce pain experienced by patient 12 in that region. In some cases, patient 12 may experience paresthesia in the dermatome where the electrodes of lead 16 are placed. However, in other cases, patient 12 may not experience paresthesia in the dermatome where the electrodes of lead 16 are placed. The stimulation of these axons or fibers may also cause antidromic action potentials that propagate toward the skin and modulate sympathetic outflow, which may reduce pain mediated by the sympathetic system, such as with some forms of complex regional pain syndrome. Lead 16 is not implanted proximate to larger, peripheral nerves in order to avoid delivery of stimulation to smaller fibers in the nerve, e.g., A-delta fibers, which may result in a patient experiencing unpleasant sensations. However, A-delta fibers may be incidentally recruited during PNFS.

By way of contrast, peripheral nerve stimulation (PNS), involves delivery of stimulation to a specific peripheral nerve via one or more electrodes implanted proximate to or in contact with a peripheral nerve, e.g., cuff electrodes surrounding the peripheral nerve. PNS may be used to deliver stimulation to, for example, the vagal nerves, cranial nerves, trigeminal nerves, ulnar nerves, median nerves, radial nerves, tibial nerves, and the common peroneal nerves. When PNS is delivered to treat pain, one or more electrodes are implanted proximate to or in contact with a specific peripheral nerve that is responsible for the pain sensation.

PNS causes orthodromic action potentials to propagate to the spinal cord via the specific peripheral nerve, diminishing pain. Typically, however, the electrodes are implanted proximate to the peripheral nerve, "upstream" from the region in which a patient perceives the pain, i.e., closer to the spinal cord than the region of pain. For PNS therapy, it is considered desirable to implant the electrodes upstream from the region in which a patient perceives pain so that the paresthesia resulting from PNS is as widely distributed as the areas innervated by the peripheral nerve, covering one or more complete dermatomes.

PNFS delivery may recruit sensory afferent nerve fibers, thereby generating an afferent response by patient 12 that results in mitigation of pain. An afferent response may include sensory physiological responses that result from nerve impulses traveling from sensory or receptor neurons toward the central nervous system. In some cases, it is believed that during delivery of PNFS to region 18 where patient 12 experiences pain, delivery of PNFS by IMD 14 activates efferent nerves. The recruitment of the efferent nerves may generate an efferent response by patient 12, which may also be an autonomic response to the PNFS. Efferent responses may include motor responses that result from nerve impulses traveling from the central nervous system to effectors, such as muscle, glands, and the like.

Efferent responses to delivery of PNFS may cause a detectable physiological effect in patient 12, which, in some cases, may be focused within region 18. For example, if PNFS is delivered to region 18 that includes muscle, the efferent response may cause muscle contractions within region 18 or proximate to region 18. As another example, if PNFS is delivered to region that includes skin or is proximate to the skin (e.g., the epidermis layer), the efferent response may include a change in cutaneous blood flow, a change in sweat gland activity (e.g., causing perspiration) or a pilomotor reflex. Accordingly, detectable efferent responses from delivery of PNFS to region 18 of patient 12 may result in a physiological effect that may be detected by monitoring a physiological parameter of patient, such as a heart rate, respiratory rate, electrodermal activity (e.g., galvanic skin response or skin conductance response), muscle activity (e.g., electromyogram (EMG)), blood flow rate, sweat gland activity, pilomotor reflex, or thermal activity of the patient's body.

Therapy system 10 includes sensing module 20, which generates a signal that changes as a function of a physiological parameter of patient 12. Sensing module 20 may include any suitable circuitry for sensing one or more physiological parameters of patient 12. The signal generated by sensing module 20 may be used to detect a physiological effect from the delivery of PNFS to patient 12 by IMD 14. The sensed physiological effect may be, but is not necessarily, an efferent response to the PNFS. In some examples, patient 12 is not conscious of the physiological effect because the physiological effect may be a relatively subtle change in a physiological parameter, such as a subtle change in the patient's muscle tone or blood flow rate. Accordingly, the PNFS therapy may cause a physiological effect that is below a threshold level for causing paresthesia, and sensing module 20 may detect the subtle physiological effect. IMD 14 or another device may control the delivery of PNFS to maintain the physiological effect that is below the level of paresthesia.

In some examples, the sensed physiological effect correlates with a desired therapeutic effect. For example, if PNFS provides efficacious therapy to patient 12 by activating muscle afferents, then changes to muscle activity of the patient 12 within region 18 may correlate well to the desired therapeutic effect. In some examples, the sensed physiological effect is coincidental to other mechanisms that relieve the patient's pain. For example, if PNFS provides efficacious therapy to patient 12 by activating sufficient numbers of A-beta fibers, then changes to the patient's skin, such as the skin conductance, blood flow rate or pilomotor reflex, may be coincidental to the PNFS therapy. As another example, if PNFS provides efficacious therapy to patient 12 by activating A-gamma fibers, then changes to the patient's muscle activity may be coincidental to the PNFS therapy. As another example, if PNFS incidentally recruits a sufficient number of A-delta or C-fibers, then the patient's thermal activity, e.g., body temperature or local tissue temperature, may be coincidental to the PNFS therapy.

As described in further detail below with reference to FIGS. 5-9, the physiological signal generated by sensing module 20 may be useful for controlling the delivery of PNFS by IMD 14, e.g., in a closed-loop therapy system, such as to activate or deactivate therapy or modify a therapy program. For example, IMD 14 may deliver therapy to patient 12 to maintain a certain physiological effect, which may be associated with a characteristic of the physiological signal, such as an amplitude of the physiological signal waveform, a trend in the physiological signal waveform, a power level of the physiological signal measured in a particular frequency band of the physiological signal waveform, ratios of power levels between different frequency bands, and the like.

Figure 16:
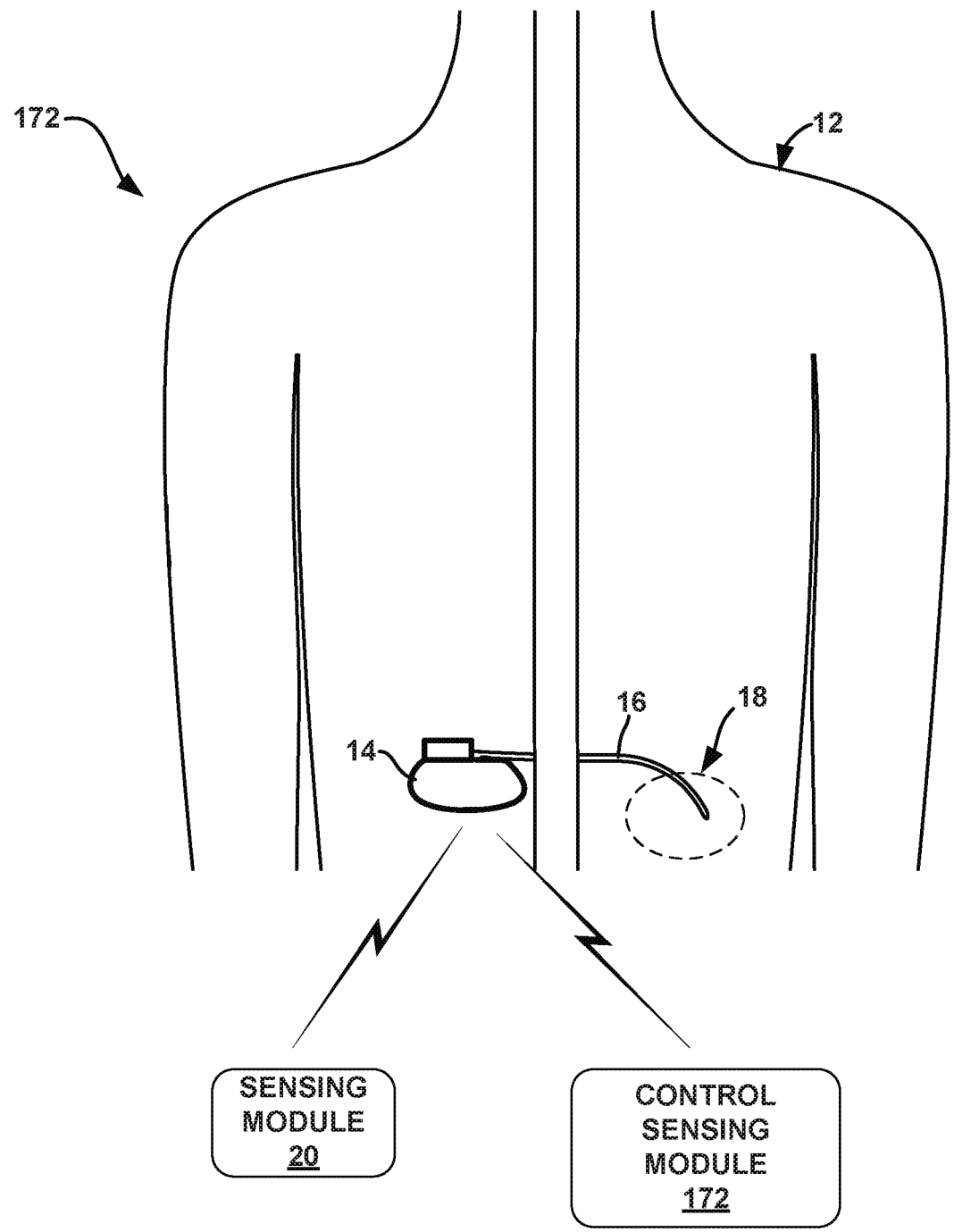
FIG. 16 is a conceptual diagram illustrating another example system for delivering PNFS to a patient.

As another example, IMD 14 may deliver therapy to patient 12 to maintain a certain physiological effect that is generally indicated by a control signal generated by a second, control sensing module (shown in FIG. 16) that senses one or more physiological parameters of patient 12. Many physiological effects from the delivery of PNFS may be relatively local in nature. For example, delivery of PNFS to region 18 may result in a change skin temperature proximate to region 18, a perspiration on a skin surface (e.g., the epidermis) within region 18, muscle activity (e.g., detectable by EMG) within region 18, and the like. Accordingly, as described with respect to FIGS. 16 and 17, in some examples, the physiological signal generated by sensing module 20 may be compared to a second physiological signal (e.g., a "control" physiological signal) in order to control the delivery of PNFS by IMD 14. The control signal may indicate the activity of the physiological parameter in a region of the patient's body that is generally does not indicate the physiological effects of the PNFS. For example, the control physiological signal may be indicative of the physiological parameter of patient in an area of the patient's body outside of region 18, In some examples, the control physiological signal is generated by a control sensing module that is separate from sensing module 20 and measures the same physiological parameter as sensing module 20. In other examples, the control physiological signal is generated by sensing module 20 or sensing module within IMD 14. As an example of the use of a control physiological signal, if therapy system 10 is implemented to minimize back spasms of patient 12, sensing module 20 may measure EMG within region 18. A second, control sensing module, as shown in FIG. 16, monitors an EMG of another region of the patient's body that does not have back spasms. A controller (e.g., a processor within IMD 14) may control IMD 14 to deliver PNFS until the physiological signal from sensing module 20 substantially matches the signal from the control sensing module.

The physiological parameter that sensing module 20 monitors may be selected based on the physiological effects of PNFS on patient 12, and may include, for example, at least one of a heart rate, respiratory rate, electro-dermal activity, muscle activity (e.g., EMG), blood flow activity, sweat gland activity, reflex responses (e.g., pilomotor reflex responses), skin conductance, or thermal activity of the patient's body. Physiological effects from PNFS may be detected by sensing other patient parameters. As described in further detail below, during a learning stage, a physiological signal characteristic may be associated with a known physiological effect.

Sensing module 20 may be external to patient 12 or may be implanted within patient 12. In addition, sensing module 20 may be coupled to IMD 14 or may be physically separate from IMD 14, as conceptually shown in FIG. 1. Thus, in some examples, sensing module 20 is incorporated within a common outer housing with the stimulation generator of IMD 14 or attached to an outer housing of IMD 14. When sensing module 20 is in a separate housing than IMD 14, sensing module 20 may be implanted within region 18, proximate to region 18, or distanced from region, depending on the physiological effect that is detected with the aid of sensing module 20. For example, to detect muscle activity within region 18, sensing module 20 may be implanted within region 18 or external to patient 12 proximate to region 18. Sensing module 20 may communicate with IMD 14 via a wired connection or via wireless communication techniques. In some examples, therapy system 10 may include sense electrodes positioned on lead 16 or one or more separate leads that are coupled to IMD 14, or electrodes on a housing of IMD 14, which may be used in addition to or instead of sensing module 20. Accordingly, while therapy system 10 including a separate sensing module 20 is primarily referred to herein, in other examples, therapy systems may include sense electrodes coupled to IM 14.

Efficacious PNFS may have an underlying effect on muscle tissue within or proximate to region 18. In some examples, sensing module 20 or sense electrodes on lead 16 or one or more separate leads detect the electrical potential generated by the patient's muscle in region 18. That is, in some examples, sensing module 20 includes one or more electrodes positioned to detect EMG signals, which may indicate changes to the patient's muscle tone (e.g., muscle contraction or relaxation) in response to PNFS. The changes in the muscle tone may not be noticeable to patient 12. Muscle tone may be sensed using any suitable type of sensor.

In addition to or instead of EMG sensing electrodes, sensing module 20 may include one or more thermal sensing electrodes positioned on the patient's skin in order to detect sweat gland activity or electrodes positioned on the patient's skin to detect an increased blood flow or pilomotor reflex responses. The increased blood flow within region 18 may also be detected by sensors positioned on leads 16, such as a laser Doppler sensor that detects blood cell velocity or an optical transmissivity measuring device that detects blood flow. In addition to or instead of the EMG or thermal sensing electrodes, sensing module 20 may include a respiration belt, an electrocardiogram (ECG) belt, implanted electrodes that measure ECG, or components that measure transthoracic impedance, which may be indicative of respiration.

System 10 also includes a clinician programmer 22. Clinician programmer 22 may, as shown in FIG. 1, be a handheld computing device. Clinician programmer 22 includes a display 24, such as a liquid crystal display (LCD) or light emitting diode (LED) display, to display information relating to PNFS and one or more of the other therapies to a user. Clinician programmer 22 may also include a keypad 26, which may be used by a user to interact with clinician programmer 22. In some examples, display 24 may be a touch screen display, and a user may interact with clinician programmer 22 via display 24. A user may also interact with clinician programmer 22 using peripheral pointing devices, such as a stylus or mouse. Keypad 26 may take the form of an alphanumeric keypad or a reduced set of keys associated with particular functions.

A clinician or physician (not shown) may use clinician programmer 22 to program PNFS for patient 12. In particular, the clinician may use clinician programmer 22 to select values for therapy parameters, such as pulse amplitude, pulse width, pulse rate, electrode polarity and duty cycle. IMD 14 may deliver the PNFS according to a therapy program that defines values for each of a plurality of such therapy parameters. In some examples, varying the pulse frequency may allow PNFS to capture target nerve fibers, such as small, medium, or large fibers sensitive to pulse frequency.

Further, IMD 14 may deliver PNFS in combination with other therapy in accordance with a program group. A program group may contain one or more programs. A program group may include one or more PNFS programs and one or more programs for the other therapy. IMD 14 may deliver stimulation pulses according to a program group by "interleaving" the pulses for each program, e.g., delivering each successive pulse according to a different one of the programs of the program group. To create programs and program groups the clinician may select existing or predefined programs, or specify programs by selecting therapy parameter values. The clinician may test the selected or specified programs on patient 12, and receive feedback from patient 12. Highly rated programs (e.g., relatively efficacious programs) may be provided to IMD 14 or a patient programmer, individually or as program groups, and used by IMD 14 to control delivery of stimulation. The clinician may identify preferred programs for PNFS and one or more other therapies separately or through delivery of the therapies together.

System 10 also includes a patient programmer 28, which also may, as shown in FIG. 1, be a handheld computing device. Patient programmer 28 may also include a display 30 and a keypad 32, to allow patient 12 to interact with patient programmer 28. In some examples, display 30 includes a touch screen display, and patient 12 interacts with patient programmer 28 via display 30. Patient 12 may also interact with patient programmer 28 using peripheral pointing devices, such as a stylus or mouse.

Patient 12 may use patient programmer 28 to control the delivery of PNFS by IMD 14. For example, patient 12 may use patient programmer 28 to activate or deactivate PNFS, and to select the programs or program group that will be used by IMD 14 to deliver PNFS. Further, patient 12 may use patient programmer 28 to make adjustments to programs or program groups. For example, upon determining that the current therapy program is ineffective at mitigating pain, patient 12 may increase the current or voltage amplitude of PNFS in order to increase the intensity of the stimulation. Patient programmer 28 may be useful, therefore, for controlling the PNFS therapy based on the patient's needs. The patient's needs may change, e.g., depending on the time of day or the current activity undertaken by patient. Additionally, the clinician or patient 12 may use programmers 22, 28 to create or adjust schedules for delivery of PNFS. As described in further detail below, in some examples, patient 12 may use patient programmer 28 or another device in order to set acceptable ranges or thresholds for certain physiological parameter values that are used in the control of IMD 14.

IMD 14, clinician programmer 22, patient programmer 28, and sensing module 20 may, as shown in FIG. 1, communicate via wireless communication. Clinician programmer 22 and patient programmer 28 may, for example, communicate via wireless communication with IMD 14 using any telemetry techniques known in the art. Such techniques may include low frequency or radiofrequency (RF) telemetry, but other techniques are also contemplated. Clinician programmer 22 and patient programmer 28 may communicate with each other using any of a variety of local wireless communication techniques, such as RF communication according to the 802.11 or Bluetooth specification sets, infrared communication according to the IrDA specification set, or other standard or proprietary telemetry protocols.

Clinician programmer 22 and patient programmer 28 may, but need not communicate wirelessly. For example, programmers 22 and 28 may communicate via a wired connection, such as via a serial communication cable, or via exchange of removable media, such as magnetic or optical disks, or memory cards or sticks. Further, clinician programmer 22 may communicate with one or both of IMD 14 and patient programmer 28 via remote telemetry techniques known in the art, communicating via a local area network (LAN), wide area network (WAN), public switched telephone network (PSTN), or cellular telephone network, for example.

Figure 2A:
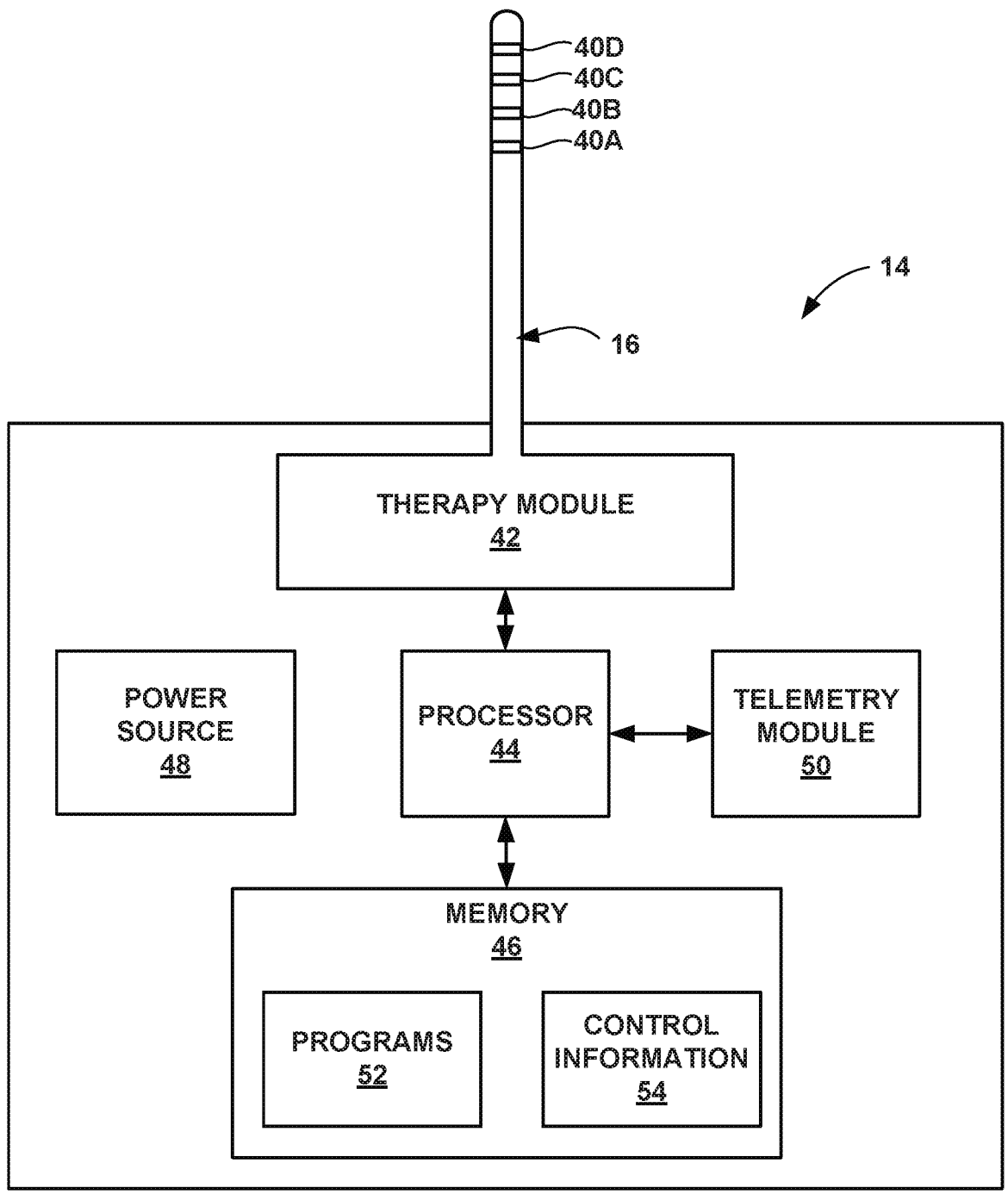
FIGS. 2A and 2B are functional block diagrams illustrating components of example implantable medical devices that deliver PNFS to a patient.

FIG. 2A is a functional block diagram illustrating components of an example of IMD 14 in greater detail. IMD 14 is coupled to lead 16, which include electrodes 40A-40D (collectively "electrodes 40"). Although IMD 14 is coupled directly to leads 16 in FIG. 2A, in other examples, IMD 14 may be coupled to lead 16 indirectly, e.g., via a lead extension. IMD 14 includes therapy module 42, processor 44, memory 46, power source 48, and telemetry module 50.

IMD 14 may deliver electrical stimulation therapy to patient 12 via electrodes 40 of lead 16. In the example shown in FIG. 2A, implantable medical lead 16 is substantially cylindrical, such that electrodes 40 are positioned on a rounded outer surface of lead 16. As previously described, in other examples, lead 16 may be, at least in part, paddle-shaped (i.e., a "paddle" lead). In some examples, electrodes 40 may be ring electrodes. In other examples, electrodes 40 may be segmented or partial ring electrodes, each of which extends along an arc less than 360 degrees (e.g., 30-120 degrees) around the outer perimeter of lead 16. The use of segmented or partial ring electrodes may also reduce the overall power delivered to electrodes 40 by IMD 14 because of the ability to more efficiently deliver stimulation to a target stimulation site by eliminating or minimizing the delivery of stimulation to unwanted or unnecessary regions within patient 12.

The configuration, type, and number of electrodes 40 illustrated in FIG. 2A are merely exemplary. For example, in other examples, IMD 14 may be coupled to one lead with eight electrodes on the lead or three or more leads with the aid of bifurcated lead extensions. Electrodes 40 are electrically coupled to a therapy module 42 of IMD 14 via conductors within lead 16. Each of the electrodes 40 may be coupled to separate conductors so that electrodes 40 may be individually selected, or in some examples, two or more electrodes 40 may be coupled to a common conductor. In one example, an implantable signal generator or other stimulation circuitry within therapy module 42 delivers electrical signals (e.g., pulses or substantially continuous-time signals, such as sinusoidal signals) to a target tissue site 18 within patient 12 via at least some of electrodes 40 under the control of processor 44. The stimulation energy generated by therapy module 42 may be delivered from therapy module 42 to selected electrodes 40 via a switching module and conductors carried by lead 16, as controlled by processor 44.

Processor 44 may include any one or more of a microprocessor, a controller, a digital signal processor (DSP), an application specific integrated circuit (ASIC), a field programmable gate array (FPGA), discrete logic circuitry, or the like, and the functions attributed to processor 44 may be embodied as software, firmware, hardware or any combination thereof. Processor 44 controls therapy delivery module 42 to deliver PNFS according to a selected one or more of therapy programs 52 stored in memory 46. In the example shown in FIG. 2A, processor 44 controls therapy module 42 to deliver electrical pulses with the amplitudes, pulse widths, frequency, or electrode polarities specified by the selected one or more therapy programs 52, which may, in some examples, be arranged into program groups. In one example, processor 44 controls therapy module 42 to deliver stimulation therapy according to one therapy program or program group at a time. In another example, therapy programs are stored within at least one of clinician programmer 22 or patient programmer 28, which transmits the therapy programs to IMD 14 via telemetry module 50. Telemetry module 50 allows processor 44 to communicate with clinician programmer 22, patient programmer 28 or another computing device.

During a trial session, which may occur after implantation of IMD 14 or prior to implantation of IMD 14, a clinician may determine the therapy parameter values that provide efficacious therapy to patient 12. Processor 44 may control therapy module 42 based on information provided by clinician programmer 22, patient programmer 28 or another computing device. For example, the clinician may interact with clinician programmer 22 to select a particular therapy program and clinician programmer 22 may transmit a control signal to IMD 14, which is received by telemetry module 50 of IMD 14. The control signal may cause processor 44 to control therapy module 42 to deliver therapy based on the parameter values specific by the clinician-selected therapy program. As another example, clinician programmer 22, patient programmer 28 or another computing device may utilize a search algorithm that automatically selects therapy programs for trialing. The search algorithm that automatically elects therapy programs for trialing may utilize one or more physiological parameters of patient sensed by sensing module 20 (FIG. 1) to select one or more stimulation parameter values for therapy delivery to patient 12.

Memory 46 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 46 may store program instructions that, when executed by processor 44, cause IMD 14 to perform the functions ascribed to IMD 14 herein. In addition to storing programs 52, memory 46 may also store control information 54, which may include information associating a characteristic of a physiological signal with a control action, such as activating or deactivating delivery of PNFS by therapy module 42 or initiating the modification of a therapy program that defines the stimulation parameter values.

The physiological signal characteristic may include, for example, an amplitude of the physiological signal waveform, a trend in the physiological signal waveform, a power level of the physiological signal measured in a particular frequency band of the physiological signal waveform, or a ratio of power levels between different frequency bands. In some examples, the physiological signal received from sensing device 20 may be compared against a threshold value in order to determine whether the physiological signal characteristic is present. The threshold comparison may, for example, be used to determine a change in the physiological signal compared to a baseline of that signal, which may be previously determined or may be a reference or control signal from a second sensor (e.g., as shown and described with respect to FIGS. 16 and 17). In other examples, the physiological signal may be compared to a template in order to determine whether the physiological signal characteristic is present in the signal from sensing module 20.

Figure 6:
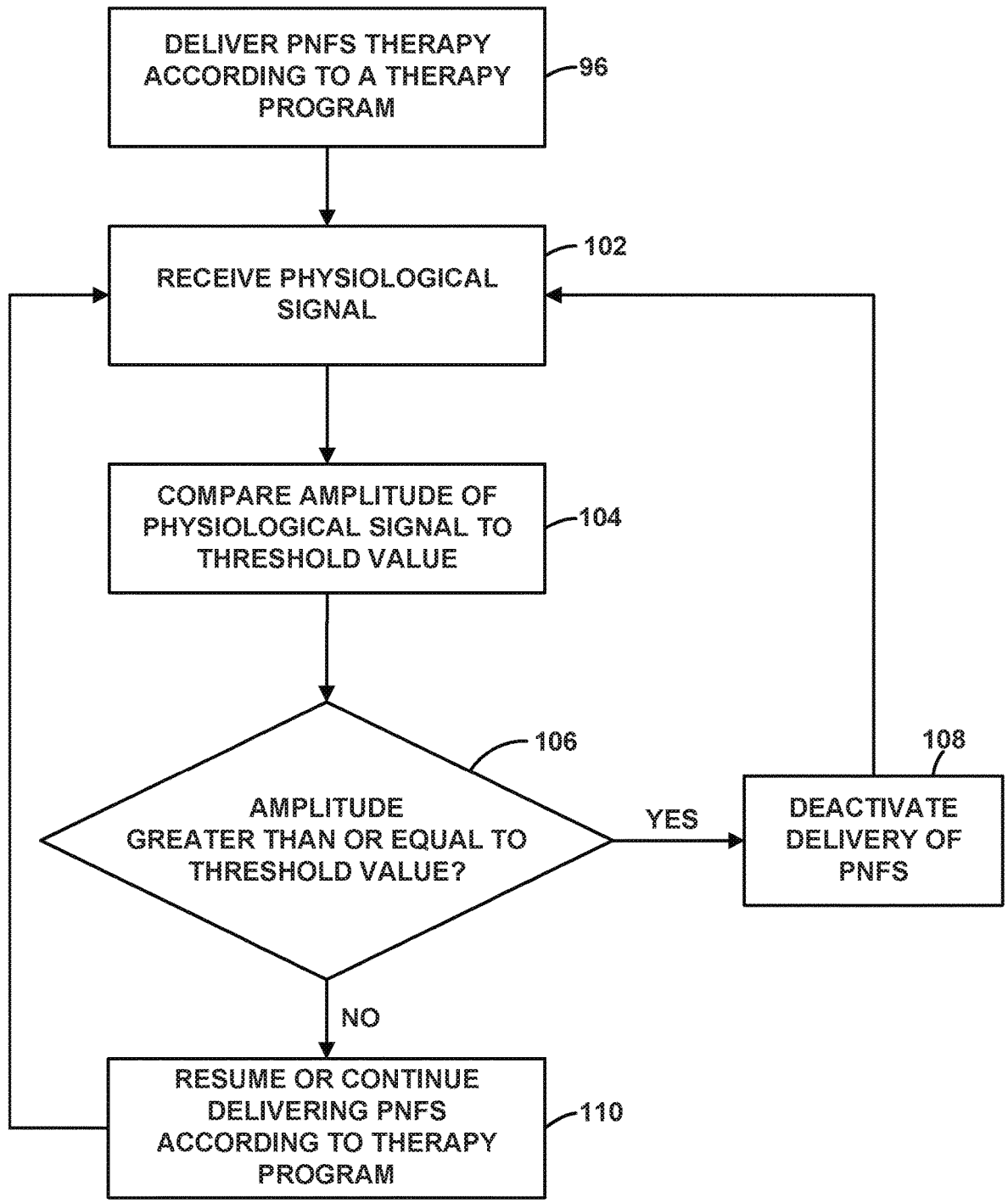

As described with respect to FIG. 6, processor 44 may use control information 54 to control therapy module 42. In some examples, memory 46 may also store patient physiological data (such as sensed physiological signals) obtained by IMD 14 or sensing module 20. Memory 46 may have any suitable architecture. For example, memory 46 may be partitioned to store therapy programs 52 and control information 54. Alternatively, therapy programs 52 and control information 54 may each be stored in separate memories that are linked to processor 44.

Power source 48 may take the form of a small, rechargeable or non-rechargeable battery, or an inductive power interface that transcutaneously receives inductively coupled energy. In the case of a rechargeable battery, power source 48 similarly may include an inductive power interface for transcutaneous transfer of recharge power.

Figure 2B:
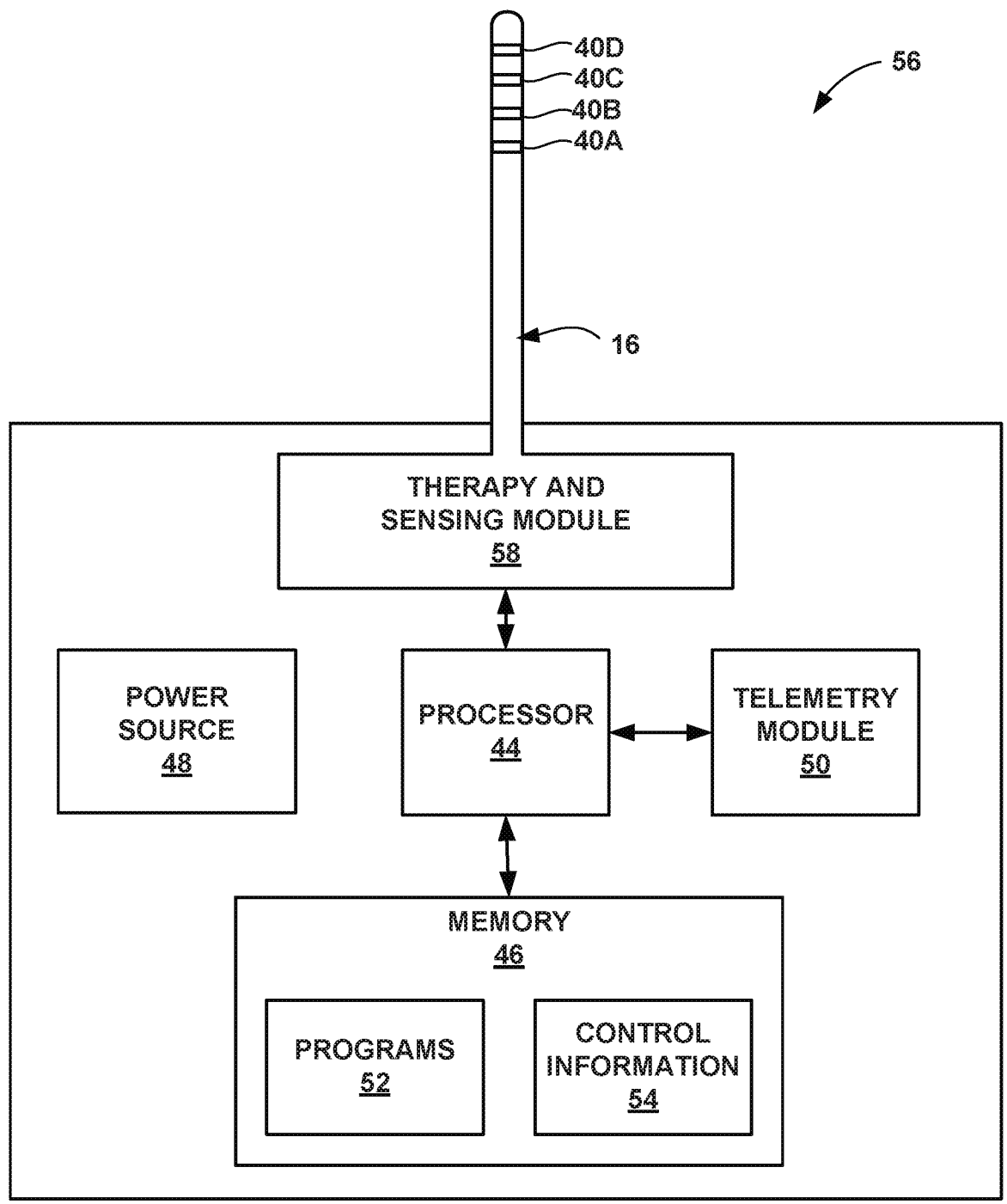

FIG. 2B is a functional block diagram of another example IMD 56, which is substantially similar to IMD 14, but includes a sensing module. As previously described, in some examples, sensing module 20 (FIG. 1) may be incorporated within a common outer housing with a therapy module of IMD 14, as shown in FIG. 2B. IMD 56 may include a therapy module and a sensing module 58 that senses a patient parameter via at least some of the electrodes 40. For example, some of electrodes 40 (or a separate set of sensing electrodes) may be used to generate an EMG signal that indicates muscle activity within region 18 of patient 12. The sensed parameter signals generated by therapy and sensing module 58 may be stored within memory 46.

In other examples, one or more additional sensors may be incorporated with IMD 56, e.g., on a housing of IMD 56 that encloses therapy and sensing module 58, processor 44, memory 46, power source 48, and telemetry module 50. In addition, in some examples, IMD 56 may communicate with an external sensing module 20 that senses the same or a different patient parameter than therapy and sensing module 58. While IMD 14 and sensing module 20 of FIG. 1 are primarily referred to throughout the description, in other examples, the disclosure is also applicable to systems including IMD 56 with therapy and sensing module 58.

Figure 3:
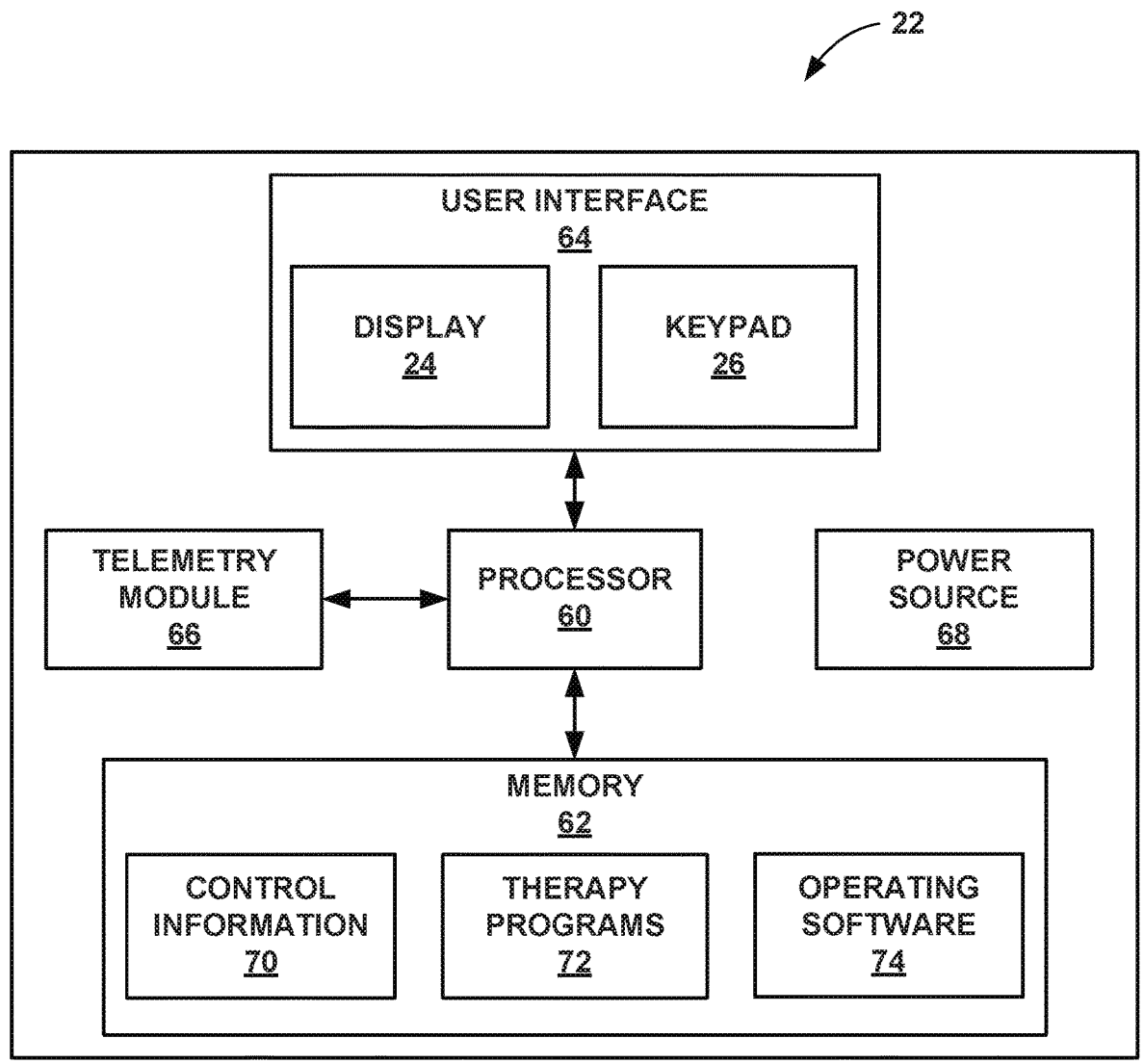
FIG. 3 is a functional block diagram illustrating components of an example clinician programmer.

FIG. 3 is a functional block diagram illustrating components of an example clinician programmer 22, which includes processor 60, memory 62, user interface 64, telemetry module 66, and power source 68. Processor 60 controls user interface 64 and telemetry module 66, and stores and retrieves information and instructions to and from memory 62. Clinician programmer 22 may be a dedicated hardware device with dedicated software for programming of IMD 14. Alternatively, clinician programmer 22 may be an off-the-shelf computing device running an application that enables programmer 22 to program IMD 14.

A clinician may use clinician programmer 22 to select therapy programs (e.g., sets of stimulation parameters), generate new therapy programs, modify therapy programs through individual or global adjustments or transmit the new programs to a medical device, such as IMD 14 (FIG. 1). The clinician may interact with programmer 22 via user interface 64, which includes display 24 and keypad 26. Keypad 26 may include any suitable mechanism for receiving input from the clinician or another user. In one example, keypad 26 includes an alphanumeric keypad. In another example, keypad 26 includes a limited set of buttons that are not necessarily associated with alphanumeric indicators. For example, the limited set of buttons may include directional buttons that permit the clinician to scroll up, down, or sideways through a display presented on display 24, select items shown on display 24, as well as enter information. The limited set of buttons may also include "increment/decrement" buttons in order to increase or decrease a stimulation frequency or amplitude of stimulation delivered by IMD 14.

Keypad 26 may include, and/or respond to, any one or more of push buttons, soft-keys that change in function depending upon the section of the user interface currently viewed by the user, voice activated commands, physical interactions, magnetically triggered functions, password authentication push buttons, contacts defined by a touch screen, or any other suitable user interface. In some examples, buttons of keypad 26 may be reprogrammable. That is, during the course of use of clinician programmer 22, the buttons of keypad 26 may be reprogrammed to provide different programming functionalities as the needs of the clinician or if the type of IMD 14 implanted within patient 12 changes. Clinician programmer 22 or another computing device may include functions for reprogramming keypad 26.

As previously discussed, display 24 may include a color or monochrome display screen, such as a LCD or LED display. Clinician programmer 22 may present information related to stimulation therapy provided by IMD 14, as well as other information, such as historical data regarding the patient's condition and past event information. Processor 60 monitors activity from keypad 26, and controls display 24 and/or IMD 14 function accordingly. In some examples, display 24 may be a touch screen that enables the user to select options directly from the display. In such cases, keypad 26 may be eliminated, although clinician programmer 22 may include both a touch screen and keypad 26. In some examples, user interface 64 may also include audio circuitry for providing audible instructions or sounds to a user and/or receiving voice commands from the user.

Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow patient data to be easily transferred to patient programmer 28, or to be removed before clinician programmer 22 is used to program PNFS therapy for a different patient.

Memory 62 stores, among other things, control information 70, therapy programs 72, and operating software 74. Memory 62 may have any suitable architecture. For example, memory 62 may be partitioned to store control information 70, therapy programs 72, and operating software 74. Alternatively, control information 70, therapy programs 72, and operating software 74 may each be stored within separate memories that are linked to processor 60. Control information 70 may be similar to the control information 54 stored in memory 46 of IMD 14 (FIG. 2A).

Therapy programs portion 72 of memory 62 stores data relating to the therapy programs implemented by IMD 14. In some examples, the actual settings for the therapy programs, e.g., the stimulation amplitude, pulse rate, pulse frequency and pulse width data, are stored within therapy programs 72. In other examples, an indication of each therapy program or group of therapy programs, e.g., a single value associated with each therapy program or group, may be stored within therapy programs 72, and the actual parameters may be stored within memory 46 of IMD 14. The "indication" for each therapy program or group may include, for example, alphanumeric indications (e.g., Therapy Program Group A, Therapy Program Group B, and so forth), or symbolic indications.

In general, during a programming session, a clinician may select values for a number of programmable therapy parameters with the aid of clinician programmer 22 in order to define the electrical stimulation therapy to be delivered by IMD 14 to patient 12. For example, the clinician may select a combination of electrodes carried by one or more implantable leads, and assigns polarities to the selected electrodes or set partial activation of electrodes in examples in which electrodes 40 of lead 16 (FIG. 2A) may be partially activated. In addition, the clinician may select an amplitude, which may be a current or voltage amplitude, a pulse width, and a pulse rate, in the case of an IMD 14 that delivers stimulation pulses to patient 12. A group of parameter values, including electrode configuration (electrode combination and electrode polarity), amplitude, pulse width and pulse rate, may be referred to as a therapy program in the sense that they drive the neurostimulation therapy to be delivered to the patient.

In some examples, the clinician may also provide information such as parameters for the IMD 14 control algorithm, such as stimulation parameter value thresholds of stimulation for patient 12 that indicate a tolerable range of PNFS, thresholds for the physiological signal characteristics that are used to control IMD 14 based on signals from sensing module 20 (or another sensing module that may be incorporated within a common housing as IMD 14), time delays or loop update frequencies for therapy delivery, or preferences for patient control (e.g., enabling or disabling a patient override of the control of system 10 based on physiological signals that may indicate a physiological effect of the PNFS).

Programs selected during a programming session using clinician programmer 22 may be transmitted to and stored within one or both of patient programmer 28 and IMD 14. Where the programs are stored in patient programmer 28, patient programmer 28 may transmit the programs selected by patient 12 to IMD 14 for delivery of PNFS therapy to patient 12 according to the selected program. Where the programs are stored in IMD 14, patient programmer 28 may receive a list of programs from IMD 14 to display to patient 12, and transmit an indication of the selected program to IMD 14 for delivery of PNFS therapy to patient 12 according to the selected program.

During a programming session, which may also be referred to as a therapy program trial session, the clinician may specify a program using clinician programmer 22 by selecting values for various therapy parameters. When a program is specified, the clinician may test the program by directing clinician programmer 22 to control MD 14 to deliver therapy according to the program to patient 12. The clinician or patient may enter rating information into the programming device for each tested program. The rating information for a tested program may include information relating to effectiveness of delivery of stimulation therapy according to the program in treating symptoms of the patient, side effects experienced by the patient due to the delivery of neurostimulation therapy according to the program, or both. In the case of stimulation therapy to manage pain, efficacy information may include an indication of the patient's activity level or a subjective rating of pain relief. If therapy system 10 provides PNFS to manage pain, control information 70 stored in memory 62 of clinician programmer 22 may include physiological parameter values that are associated with a particular patient pain state.

During the programming session, multiple therapy programs may be tested. That is, during a programming session, IMD 14 may deliver therapy to patient 12 according to a first therapy program, followed by a second therapy program, and so forth, in order to assess the efficacy of each therapy program. Clinician programmer 22 may maintain a session log that includes a listing of programs tested on patient 12, rating information provided by the clinician or patient 12 for programs of the list, and control information, such as information that associates a particular patient parameter value with a positive patient response to therapy (e.g., an improvement from the patient's baseline state). The listing of trialed therapy programs may be ordered according to the rating information in order to facilitate the selection of programs from the list by the clinician.

Operating software 74 may include instructions executable by processor 60 for operating user interface 64, telemetry module 66, and managing power source 68. Memory 62 may also store any therapy data retrieved from IMD 14 during the course of therapy and store any data received from patient programmer 28. The clinician may use this therapy data to determine the progression of the patient's disease in order to predict or plan a future treatment.

Clinician programmer 22 may communicate via wireless telemetry with IMD 14, such as using RF communication or proximal inductive interaction. This wireless communication is possible through the use of telemetry module 66. Accordingly, telemetry module 66 may be similar to telemetry module 50 of IMD 14. Telemetry module 66 may also be configured to communicate with patient programmer 28 or another computing device via wireless communication techniques, or direct communication through a wired connection. Examples of local wireless communication techniques that may be employed to facilitate communication between clinician programmer 22 and another computing device include RF communication according to the 802.11 or Bluetooth specification sets, infrared communication, e.g., according to the IrDA standard, or other standard or proprietary telemetry protocols. In this manner, other external devices may be capable of communicating with clinician programmer 22 without needing to establish a secure wireless connection.

Power source 68 delivers operating power to the components of clinician programmer 22. Power source 68 may include a battery and a power generation circuit to produce the operating power. In some examples, the battery may be rechargeable to allow extended operation. Recharging may be accomplished by electrically coupling power source 68 to a cradle or plug that is connected to an alternating current (AC) outlet. In addition, recharging may be accomplished through proximal inductive interaction between an external charger and an inductive charging coil within clinician programmer 22. In other examples, traditional batteries (e.g., nickel cadmium or lithium ion batteries) may be used. In addition, clinician programmer 22 may be directly coupled to an alternating current outlet to recharge power source 68, or to power clinician programmer 22. Power source 68 may include circuitry to monitor power remaining within a battery. In this manner, user interface 64 may provide a current battery level indicator or low battery level indicator when the battery needs to be replaced or recharged. In some cases, power source 68 may be capable of estimating the remaining time of operation using the current battery.

Figure 4:
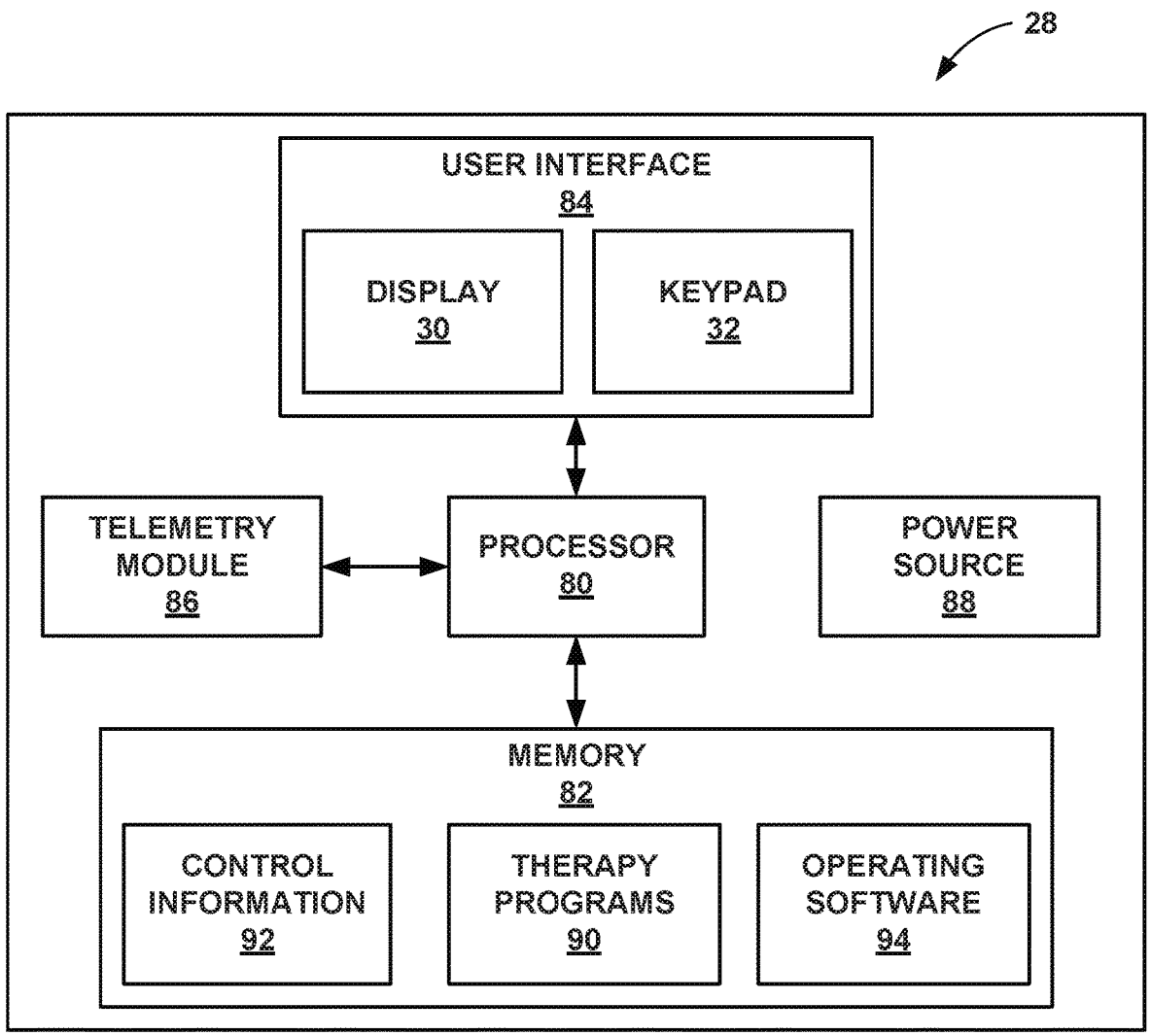
FIG. 4 is a functional block diagram illustrating components of an example patient programmer.

FIG. 4 is a functional block diagram illustrating components of patient programmer 28, which may be similar to clinician programmer 22. Patient programmer 28 may include a processor 80, memory 82, user interface 84, which includes display 30 and keypad 32, telemetry module 86, and power source 88. Memory 82 stores therapy programs 90, control information 92, and operating software 94. Memory 82 may have any suitable architecture. For example, memory 82 may be partitioned to store control therapy programs 90, control information 92, and operating software 94. Alternatively, therapy programs 90, control information 92, and operating software 94 may each be stored within separate memories that are linked to processor 80. Control information 92 may be similar to the control information 54 stored in memory 46 of IMD 14 (FIG. 2A).

The functions performed by each component of patient programmer 28 shown in FIG. 4 may be similar to the functions described above with reference to the similar components of clinician programmer 22. However, clinician programmer 22 may include more features than patient programmer 28. For example, clinician programmer 22 may be configured for more advanced programming features than patient programmer 28. This may allow a user to modify more therapy parameters with clinician programmer 22 than with patient programmer 28. Patient programmer 28 may have a relatively limited ability to modify therapy parameters of IMD 14 in order to minimize the possibility of patient 12 selecting therapy parameters that may be harmful to patient 12. Similarly, clinician programmer 22 may conduct more advanced diagnostics of IMD 14 than patient programmer 28.

Patient 12 may interact with patient programmer 28 via user interface 84, which includes display 30 and keypad 32. Patient 12 may input information via user interface 84 relating to the therapeutic efficacy of a therapy program or a patient state during therapy delivery by IMD 14 according to a particular therapy program. In some cases, patient programmer 28 provides patient 12 with an option of enabling or disabling automatic control of IMD 14, or override it with other preferences, e.g., depending on the patient's pain state. The information relating to the patient state may be used to control therapy delivery by IMD 14. As described in further detail below, patient 12 may input information indicating a patient pain state via user interface 84. The patient pain state information may then be used to control therapy delivery by IMD 14.

It is believed that delivery of PNFS by IMD 14 generates a detectable change in a physiological parameter of patient 12 that indicates the physiological effect of the PNFS on patient 12. In order to maintain efficacious PNFS therapy, it may be desirable for IMD 14 to deliver PNFS to patient 12 to maintain the physiological effect, or, in some cases, avoid the physiological effect if the physiological effect is an undesirable side effect. In some examples, the physiological effect is maintained by controlling the PNFS such that an amplitude or energy level in one or more frequency bands of a physiological signal remains at a certain level, within a range of values, below a certain level or above a certain level, depending on the physiological parameter. The desired level of the physiological signal characteristic may be determined based on information received during a programming session in which patient input regarding therapeutic efficacy (e.g., balance of beneficial results and side effects) is received in response to therapy delivery and associated with a physiological signal characteristic. In other examples, desired level of the physiological signal characteristic may be determined based on a control signal from a second sensing module (shown in FIG. 16), which indicates a desirable value for the physiological signal characteristic.

As another example, the physiological effect may be maintained by controlling PNFS such that a physiological signal waveform maintains some trend (e.g., a particular slope), which may depend upon the type of physiological effect. Accordingly, processor 44 of IMD 14 may control therapy module 42 based on a physiological signal generated by sensing module 20.

While processor 44 of MD 14 is primarily referred to in the description of FIGS. 5-9, in other examples, processor 60 of clinician programmer 22, processor 80 of patient programmer, or a processor of another device may control therapy module 42 based on a physiological signal generated by sensing module 20. Furthermore, while the reminder of the description primarily refers to IMD 14 and a separate sensing module 20, in other examples, therapy system 10 may be controlled based on a physiological signal that is sensed by an IMD (e.g., IMD 56 in FIG. 2B) in addition to or instead of the signal generated by sensing module 20.

Figure 5:
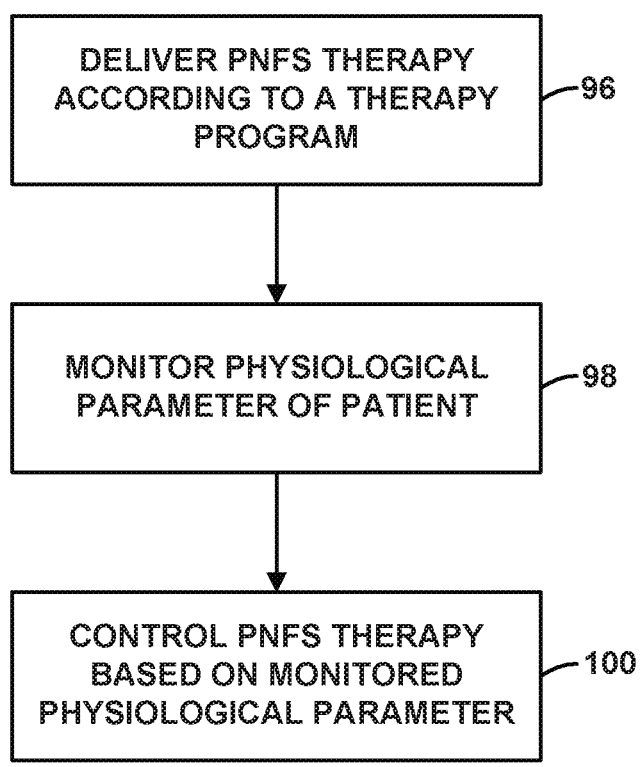
FIGS. 5-9 are flow diagrams illustrating example techniques for controlling an implantable medical device based on a sensed physiological parameter of a patient.

FIG. 5 is a flow diagram illustrating an example technique for controlling therapy system 10 based on a sensed physiological parameter of patient 12 that indicates the physiological effects (e.g., an efferent response) of the PNFS on patient 12. Processor 44 controls therapy module 42 to deliver PNFS to region 18 (FIG. 1) of patient 12 according to a therapy program (96). For example, processor 44 may select a therapy program from memory 46 of IMD 14 and control therapy module 42 to generate and deliver according to the selected therapy program. As another example, processor 44 may control therapy module 42 to deliver PNFS according to a clinician-selected therapy program. In one example, the clinician may select the therapy program from a list of therapy programs stored in clinician programmer 22 (FIG. 3) by interacting with user interface 64. Processor 60 of clinician programmer 22 may then transmit a control signal to processor 44 of IMD 14 by the telemetry module 66 of clinician programmer 22. The control signal may set forth the parameter values of the therapy program or may merely be an identifier associated with the therapy program, and the actual parameter values may be stored within memory 46 of IMD 14 and associated with the identifier in memory 46.

In another example, processor 44 controls therapy module 42 to deliver PNFS according to a patient-selected therapy program. For example, patient 12 may select the therapy program from a list of therapy programs stored in memory 82 of patient programmer 28 (FIG. 4) by interacting with user interface 84. Processor 80 of patient programmer 28 may then transmit a control signal to processor 44 of IMD 14 via the respective telemetry modules 86 (FIG. 4), 50 (FIG. 2A). Again, the control signal may define the therapy parameter values or may merely be an identifier associated with a therapy program that is stored in IM 14.

Processor 44 monitors a physiological parameter of patient 12, such as by receiving a physiological signal from sensing module 20 (FIG. 1) (98). As previously indicated, the physiological signal may indicate an efferent response of the patient to the PNFS. Processor 44 controls therapy module 42 based on the monitored physiological parameter of patient 12 (100). In some examples, processor 44 activates or deactivate therapy delivery or modifies the therapy program, e.g., if processor 44 determines that the physiological signal indicates the therapy program is not efficacious or does not meet a certain level of efficacy.

In this way, the patient's efferent response to PNFS, detected by monitoring a physiological parameter of patient 12, may be used in a closed-loop therapy system in order to control the therapy delivery. The detected efferent response may be incidental to the PNFS because IMD 14 may deliver PNFS to patient 12 to generate an afferent response, and may incidentally activate efferent nerves, thereby resulting in an efferent response from the patient. Examples of efferent responses include muscle contractions, a change in blood flow, activation of the sweat glands or a pilomotor reflex response (e.g., goose bumps).

In some examples, processor 44 monitors more than one physiological parameter of patient 12 at a time (98) and control therapy delivery by therapy module 42 (FIG. 2) based on the plurality of monitored physiological parameters. For example, processor 44 may receive more than one physiological signal from sensing module 20, whereby the different signals indicate the activity of respective physiological parameters. Processor 44 may control the delivery of therapy to patient 12 to maintain a physiological effect that is based on the plurality of monitored physiological parameters. For example, processor 44 may control the delivery of PNFS such that respective signal characteristics of the one or more physiological parameters remain within respective ranges, at respective levels, above or below respective levels (depending upon the type of physiological parameter), at some level relative to respective control signals, exhibit respective predetermined trends, and the like. For example, processor 44 may control therapy module 42 to deliver PNFS to region 18 such that a physiological signal indicative of the blood flow rate through region 18 is increased, but is not increased so high that an amplitude of another physiological signal indicative of a pilomotor response is greater than or equal to a threshold value.

In some examples, the plurality of monitored physiological parameters may be weighted, such that processor 44 may assign a higher priority to controlling PNFS therapy to control a particular physiological parameter of the plurality of monitored physiological parameters.

In various examples, processor 44 may perform template matching, peak detection, or threshold amplitude or energy level value comparisons in order to determine the patient's physiological response to the PNFS and control therapy. Example techniques processor 44 may employ to determine the patient's response to PNFS are described with reference to FIGS. 6-9.

FIG. 6 is a flow diagram illustrating an example technique for controlling therapy system 10 based on an amplitude of a physiological signal. Just as in the technique shown in FIG. 5, processor 44 of IMD 14 controls the delivery of PNFS therapy to patient 12 according to a therapy program (96). Processor 44 receives a physiological signal from sensing module 20 (102). As therapy is delivered to patient 12, processor 44 determines a physiological effect on patient 12 by comparing an amplitude of the received physiological signal to a threshold value (104). The threshold value may be stored within control information portion 54 of memory 46 or may be determined based on a control physiological signal that indicates the activity of the physiological parameter in another region of the patient's body that is outside of region 18 (FIG. 1) to which PNFS is delivered. The latter technique for determining a threshold value based on a control physiological signal is described below with reference to FIGS. 16 and 17. The control physiological signal may be generated by a control sensing module that is separate from sensing module 20 or may be generated by sensing module 20 or IMD 14.

In one example, processor 44 samples the physiological signal, e.g., using a 5 ms to a 10 second time window, and compares a peak, average or median amplitude during the sample time window to the threshold window (104). The time window may be selected based on the cycle of the selected physiological parameter. For example, when monitoring respiratory rate, the window may be about 3 seconds to about 10 seconds because a respiratory cycle may take about 3 seconds to about 10 seconds, although other cycles are contemplated. As another example, when monitoring muscle activity via EMG signals, the EMG signals may change relatively fast (e.g., within about 5 ms to about 10 ms of providing PNFS). Processor 44 may perform the amplitude-threshold comparison at any suitable frequency, such as about 0.1 Hertz (Hz) to about 15 Hz or greater. For example, some examples of processor 44 may perform the amplitude-threshold comparison at a frequency of up to 500 Hz.

In one example, a desired therapeutic effect may be associated with a particular characteristic of a physiological parameter of the patient, and therapy may be delivered to the patient until the physiological parameter characteristic is detected. If processor 44 determines that the amplitude of the physiological signal is greater than or equal to the threshold value (106), processor 44 may determine that the patient's response to the delivery of PNFS was positive, e.g., IMD 14 provided efficacious therapy. Accordingly, processor 44 deactivates the delivery of PNFS if the amplitude of the physiological signal is greater than or equal to the threshold value (108). Processor 44 may then continue monitoring the physiological signal (102) and comparing the signal amplitude to the threshold value in order to determine when the positive physiological effects of the PNFS have substantially dissipated, as indicated by a signal amplitude value that is not greater than or equal to a threshold value. At that time, processor 44 initiates the delivery of PNFS therapy according to the therapy program (110). In other examples, rather than deactivating the delivery of PNFS (108), processor 44 decreases the intensity of stimulation, such as by decreasing an amplitude of the electrical stimulation signal defined by the therapy program or the duration of the signal, or modifying the frequency, duty cycle or pulse width of the stimulation signal.

Rather than delivering continuous PNFS to patient 12, processor 44 controls therapy module 42 to provide therapy to patient as needed, i.e., on-demand, based on the physiological signal indicative of the effects of the PNFS. The on-demand therapy may be a more efficient use of power source 48 (FIG. 2A) of IMD 14 compared to continuous delivery of PNFS. In addition, the therapy delivery technique described with respect to FIGS. 5 and 6, as well as the techniques described with respect to FIGS. 7-9, may help reduce the possibility or speed at which patient 12 adapts to the PNFS therapy. It has also been found that patient 12 may adapt to PNFS provided by IMD 14 over time. That is, a certain level of electrical stimulation provided to region may be less effective over time. This phenomenon may be referred to as "adaptation" or "accommodation." As a result, any beneficial effects to patient 12 from the PNFS may decrease over time. While the electrical stimulation levels (e.g., amplitude of the electrical stimulation signal) may be increased to overcome such adaptation, the increase in stimulation levels may consume more power, and may eventually reach undesirable or harmful levels of stimulation.

If processor 44 determines that the amplitude of the physiological signal is not greater than or equal to the threshold value (106), processor 44 may determine that the therapeutic effects of the PNFS have not been achieved yet. Accordingly, processor 44 controls therapy module 42 to continue delivering PNFS according to the therapy program (110). Processor 44 may continue monitoring the physiological signal and comparing the signal to the threshold value to determine when to deactivate the PNFS (108).

In other examples, rather than determining a physiological effect of the PNFS therapy on patient 12 as the PNFS is delivered to patient 12, processor 44 may control the delivery of therapy to patient 12 for a particular time period, such as 30 seconds to an hour or more, and determine the physiological effect after the PNFS delivery time period (i.e., the "stimulation period") and while the delivery of PNFS to patient 12 is suspended. If, after the stimulation period, the amplitude of the physiological signal is less than the threshold value, processor 44 may control therapy module 42 to deliver therapy to patient 12 for a subsequent stimulation period. After the subsequent stimulation period, processor 44 may compare the amplitude of a received physiological signal to the threshold value. In this way, processor 44 may control therapy delivery based on a cycle including a stimulation period followed by an analysis time period during which PNFS is not delivered or has a reduced intensity to assess the patient's physiological response to the therapy.

In another example of FIG. 6, rather than deactivating therapy if the amplitude of the physiological signal is greater than or equal to the threshold value, processor 44 may deactivate therapy if the amplitude of the physiological signal is within an acceptable range of values, which may also be stored within control information 54 portion of memory 46.

Furthermore, although in FIG. 6, processor 44 determines that therapeutic effects of the PNFS are present when the amplitude of the physiological signal is greater than or equal to a threshold value, in other examples, depending on the type of physiological signal, processor 44 may determine that therapeutic effects of the PNFS are present when the amplitude is greater than the threshold value, or less than the threshold value or less than or equal to the threshold value. For example, if therapy system 10 is implemented to mitigate pain due to back spasms, the physiological signal may indicate EMG activity of region 18 (FIG. 1). Processor 44 may determine that positive physiological effects of the PNFS are observed when the back spasms have subsided, which may be associated with a physiological signal amplitude less than or equal to the threshold value.

Figure 7:
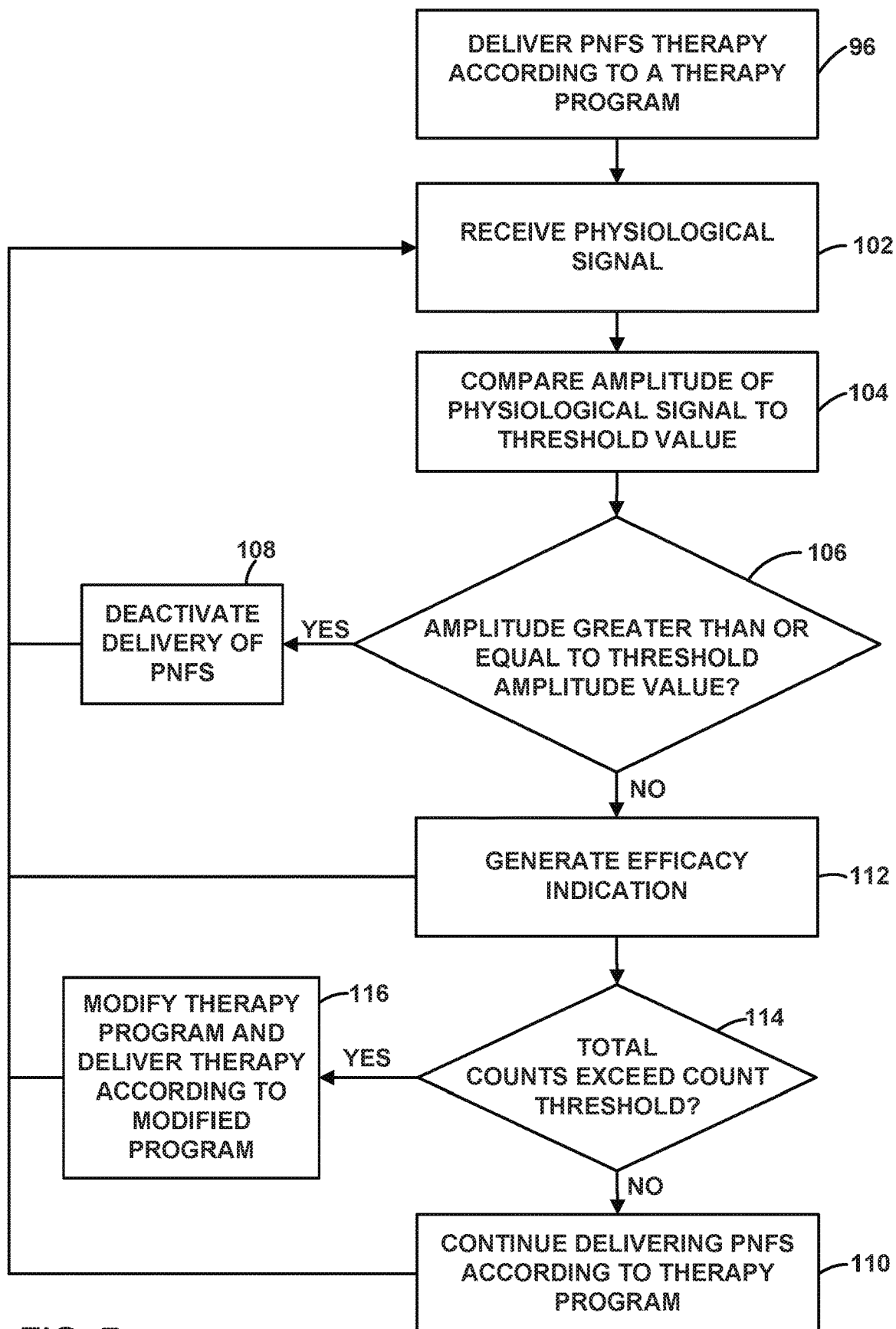

In some cases, a selected therapy program may be ineffective. For example, as discussed above, in some cases, patient 12 may adapt to PNFS and the intensity of stimulation (e.g., the amplitude or another stimulation parameter) may be increased in order to maintain therapeutic effects. FIG. 7 is a flow diagram of an example technique for modifying a therapy program based on detected physiological effects of PNFS. The technique shown in FIG. 7 is similar to the technique shown in FIG. 6. However, after determining that the amplitude of the physiological signal is not greater than or equal to the threshold amplitude value (106), processor 44 generates and stores an efficacy indication, which may be a value, flag, or signal that is stored or transmitted to indicate the therapy program was not effective (112).

Different patients may respond differently to PNFS. For some patients, therapeutic effects of the therapy delivery may not be immediate, and may be observed after PNFS is delivered for a particular time period, such as a few minutes, a few hours or even a day or more. Accordingly, processor 44 may not immediately modify a therapy program if therapeutic effects are not observed. Instead, processor 44 may compare a total efficacy indication count, which may be stored in memory 46 of IMD 14 or a memory of another device, to a count threshold value, which may also be stored in memory 46 or another device. In some examples, the threshold efficacy count for triggering the modification to the therapy program may be selected by the clinician.

If the efficacy indication count does not exceed the count threshold (114), processor 44 may continue delivering PNFS therapy according to the selected therapy program (110) and monitoring the physiological signal (102) to determine if a physiological response of patient 12 indicates the PNFS was efficacious. The efficacy count may reflect the total number of efficacy indications within a particular time period, such as the entire duration the therapy was delivered according to the therapy program or a more limited time period, such as a day or more.

On the other hand, if the efficacy indication count is greater than or equal to the count threshold (114), processor 44 determines that the selected therapy program is not efficacious. Accordingly, processor 44 modifies the therapy program (116) if the efficacy count exceeds (or is greater than or equal to) the threshold. Processor 44 may modify the therapy program using any suitable technique. In one example, processor 44 selects another therapy program from memory 46. For example, the therapy programs 52 stored in memory 446 may be ordered according to their relative efficacy. Processor 44 may select the next-best therapy program from the stored therapy programs 52 upon determining that the current therapy program is ineffective.

In another example, processor 44 may notify processor 60 of clinician programmer 22 (FIG. 3) that a modification to the therapy program is desirable, and processor 60 of programmer 22 may implement a methodical system to identify another set of potentially beneficial therapy parameter values for patient 12. In one example, processor 60 may implement a tree-based technique for selecting the therapy program. A programming tree structure may include a plurality of levels that are associated with a different therapy parameter. The tree may include nodes that are connected to nodes of adjacent levels. A clinician or patient 12 may interact with processor 60 via user interface 64 (FIG. 3) in order to create a program path by moving through one node at each level of the tree according to efficacy feedback from patient 12 and/or one or more sensors that detect physiological parameters of patient 12, such as sensing module 20.

Examples of tree-based techniques for modifying a therapy program or generating a new therapy program are described in commonly-assigned U.S. patent application Ser. No. 11/799,114 to Gerber et al., entitled, "TREE-BASED ELECTRICAL STIMULATION PROGRAMMING FOR PAIN THERAPY," and filed on Apr. 30, 2007; commonly-assigned U.S. patent application Ser. No. 11/799,113 to Gerber et al., entitled, "TREE-BASED ELECTRICAL STIMULATOR PROGRAMMING," and filed on Apr. 30, 2007; and commonly-assigned U.S. patent application Ser. No. 11/414,527 to Gerber et al., entitled, "TREE-BASED ELECTRICAL STIMULATOR PROGRAMMING," and filed on Apr. 28, 2006, which are each incorporated herein by reference in their entireties.

In another example, processor 60 of clinician programmer 22 may implement a genetic algorithm-based technique for modifying the therapy program, such as the one described in commonly-assigned U.S. Pat. No. 7,239,926 to Goetz et al., entitled, "SELECTION OF NEUROSTIMULATION PARAMETER CONFIGURATIONS USING GENETIC ALGORITHMS," which issued on Jul. 3, 2007 and is incorporated herein by reference in its entirety. In one example described in U.S. Pat. No. 7,239,926 to Goetz et al., genetic algorithms guide the selection of stimulation parameter values by suggesting the parameter values that are most likely to be efficacious given the results of tests already performed during an evaluation (or programming) session. Genetic algorithms encode potential solutions to a problem as members of a population of solutions. This population is then judged based on a fitness function. The best performers, i.e., the best fit solutions, are then retained and a new generation is created based upon their characteristics. The new generation is composed of solutions similar in nature to the best performers of the previous generation.

Other suitable techniques for selecting a therapy program include those described in U.S. Pat. No. 7,184,837 to Goetz, entitled, "SELECTION OF NEUROSTIMULATOR PARAMETER CONFIGURATIONS USING BAYESIAN NETWORKS," which was filed on Jan. 29, 2004 and is incorporated herein by reference in its entirety. As described in U.S. Pat. No. 7,184,837 to Goetz, processor 60 of clinician programmer 22 or another device, or a clinician may execute a parameter configuration search algorithm that relies on a Bayesian network structure that encodes conditional probabilities describing different states of the parameter configuration. The Bayesian network structure may provide a conditional probability table that represents causal relationships between different parameter configurations and clinical outcomes. The search algorithm uses the Bayesian network structure to infer likely efficacies of possible parameter configurations based on the efficacies of parameter configurations already observed.

Processor 60 of clinician programmer 22 may transmit the modified therapy program to IMD 14, and processor 44 of IMD 14 may control therapy module 42 to deliver PNFS therapy to patient 12 according to the modified therapy program (116). Processor 44 may then monitor the physiological effects of the PNFS according to the modified program by monitoring the physiological signal (102) and comparing the signal to a threshold (106). The technique shown in FIG. 7 may then be implemented for the modified therapy program.

In some examples, processor 44 generates a notification to alert patient 12 that the therapy program was modified. For example, processor 44 may transmit an alert to patient programmer 28 via telemetry module 50 that is provided to patient 12 via user interface 84 of patient programmer 28 (FIG. 4). The alert may be a visual, auditory or somatosensory (e.g., vibration) alert. In addition, processor 44 may record the therapy modification in memory 46 or in memory 82 of patient programmer 28 or another device for later analysis by the clinician.

Figure 8:
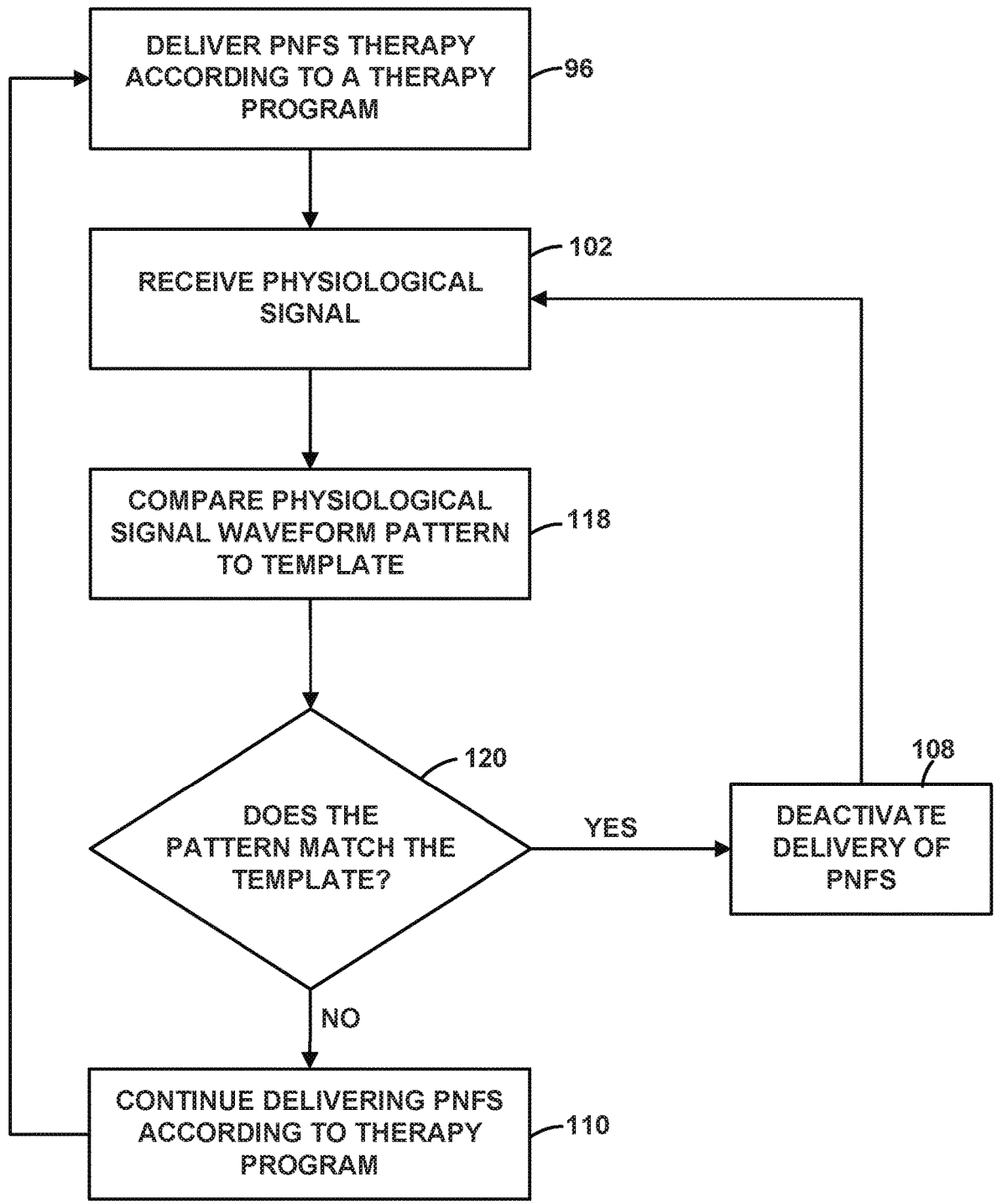

FIG. 8 is a flow diagram of an example technique for controlling therapy system 10 based on a pattern in a physiological signal waveform, where the pattern is indicative of the therapeutic efficacy of the PNFS. Just as with the techniques shown in FIGS. 6 and 7, processor 44 of IMD 14 controls therapy module 42 to deliver PNFS therapy according to a therapy program (96) and receives a physiological signal from sensing module 20 (102).

As previously indicated, processor 44 may control therapy module 42 to deliver PNFS in order to maintain a particular a physiological effect of the PNFS. In the example technique shown in FIG. 8, the physiological effect is characterized by one or more characteristics (e.g., a pattern) of a physiological signal waveform. Accordingly, during or after a stimulation period during which therapy module 42 delivers PNFS to patient 12, processor 44 compares a physiological signal waveform to a template (118) in order to determine whether to continue delivering PNFS or to deactivate PNFS. The template may be stored in control information 54 portion of memory 46 of IMD 14. In some examples, the template is determined during a programming session in which a clinician associates a physiological signal characteristic (e.g., the template) with a desirable physiological response or an undesirable physiological response. In other examples, the template is determined based on a control physiological signal that indicates the activity of the physiological parameter of the patient in a region outside of the region 18 in which patient 12 feels pain.

In one example, processor 44 implements a temporal correlation technique, during which processor 44 samples the physiological signal waveform with a sliding window and compares the sample to a template to determine whether the sampled signal correlates well with the template. For example, processor 44 may perform a correlation analysis by moving a window along a digitized plot of the amplitude of the measured physiological signals at regular intervals, such as between about 1 ms to about 1 second intervals, to define a sample of the physiological signal. The sample window may be slid along the plot of the physiological signal waveform until a correlation is detected between the waveform of the baseline template and the waveform of the sample of the physiological signal defined by the window.

By moving the window at regular time intervals, multiple sample periods are defined. The correlation may be detected by, for example, matching multiple points between the template waveform and the waveform of the plot of the physiological signal over time, or by applying any suitable mathematical correlation algorithm between the sample in the sampling window and a corresponding set of samples stored in the template waveform. As examples, if rate of change (i.e., the slope) of the monitored physiological signal correlates to the slope of a trend template, the physiological signal may indicate the presence of positive therapeutic effects of the PNFS therapy. As another example, if inflection points in the physiological signal waveform substantially correlate to a template, the physiological signal may indicate the presence of positive therapeutic effects of the PNFS therapy.

If the pattern in the physiological signal waveform substantially matches the template (120), processor 44 deactivates the delivery of PNFS (108) until the physiological signal indicates therapy delivery is desirable, e.g., a pattern of the physiological signal waveform no longer matches the template. In some examples, the template matching algorithm that processor 44 employs to determine whether the pattern in the physiological signal substantially matches the template may not require a one hundred percent (100%) correlation match, but rather may only match some percentage of the pattern. For example, if the monitored physiological signal exhibits a pattern that matches about 75% or more of the template, processor 44 may determine that there is a substantial match between the pattern and the template.

On the other hand, if the pattern in the physiological signal waveform does not substantially match the template (120), processor 44 continues delivering PNFS to patient 12 according to the therapy program. In some examples, processor 44 may generate an efficacy indication and modify the therapy program if a total count of the efficacy indications exceeds a threshold value, as discussed with respect to FIG. 7.

In other examples, rather than deactivating the delivery of PNFS (108), processor 44 may decrease the intensity of stimulation, such as by decreasing an amplitude of the electrical stimulation signal defined by the therapy program, decreasing the duration of the stimulation signal, decreasing the frequency, or changing the pulse burst pattern. In addition, in the technique shown in FIG. 8, processor 44 deactivates therapy delivery if the physiological signal waveform matches a template, while in other examples, processor 44 decreases the intensity of PNFS provided to region 18. In other examples, however, processor 44 deactivates therapy delivery if the physiological signal waveform does not match a template and continues controlling therapy module 42 to deliver PNFS to region 18 of patient 12 if the waveform matches the template.

Figure 9:
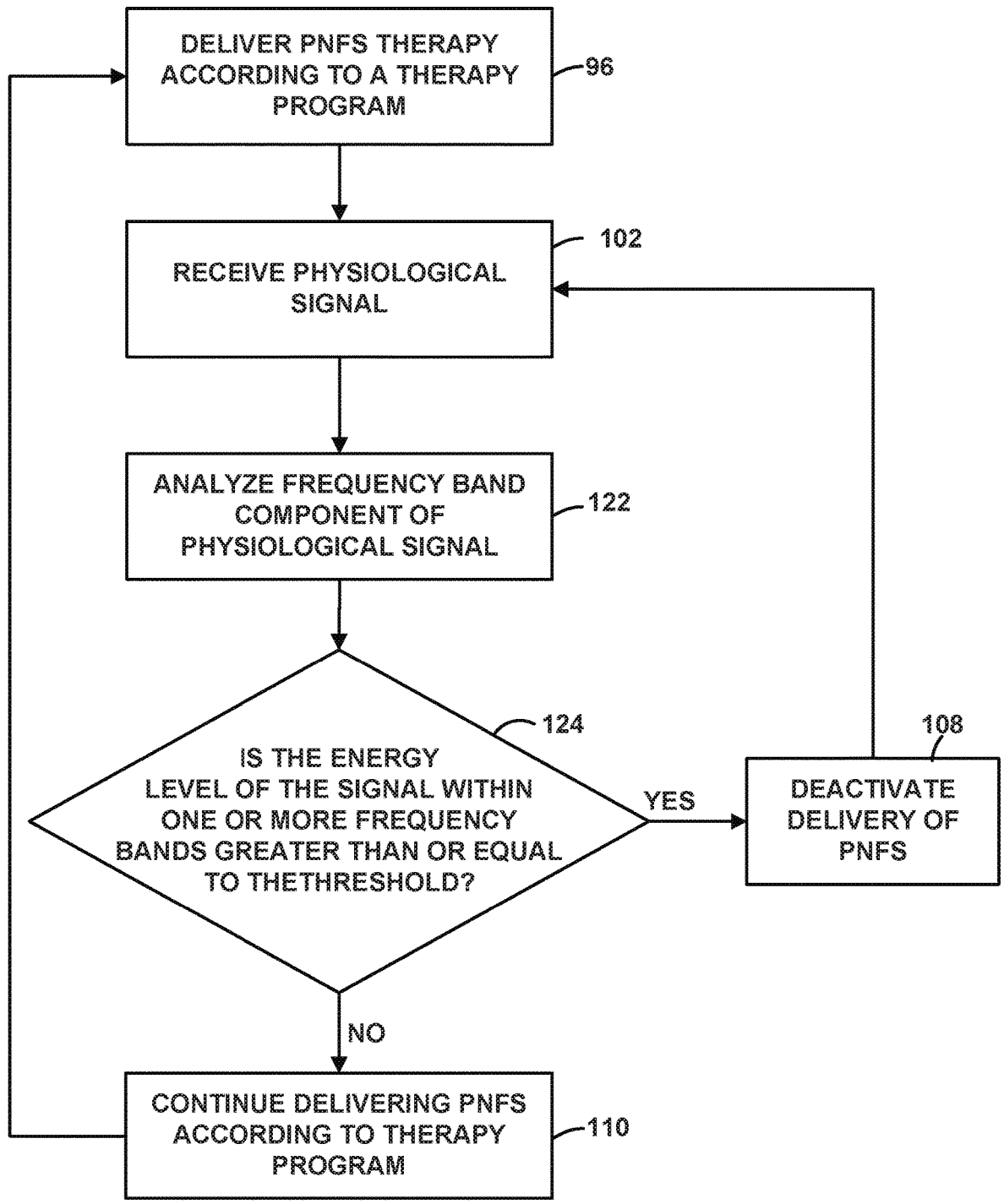

FIG. 9 is a flow diagram of an example technique for controlling therapy system 10 based on a frequency band (or frequency domain) component of a physiological signal that indicates a patient's physiological response to the PNFS. Just as with the techniques shown in FIGS. 6-8, processor 44 of IMD 14 controls therapy module 42 to deliver PNFS therapy according to a therapy program (96) and receives a physiological signal from sensing module 20 (102) that changes as a function of a selected physiological parameter of patient 12.

Processor 44 analyzes the physiological signal in the frequency domain (122) and compares one or more selected frequency components of the physiological signal to corresponding frequency components of a template signal, which may be stored in memory 46 of MD 14, a memory of another device or may be based on a control physiological signal that indicates the activity of the selected physiological parameter outside of the region 18 in which patient 12 feels pain. Either sensing module 20 or processor 44 may tune the physiological signal to a particular frequency band, which may be selected based on the frequency band that is most revealing of the physiological effects from PNFS. Processor 44 compares an energy level within the particular frequency band to a stored value to determine whether the PNFS resulted in beneficial physiological effects within patient 12 (124). In another example, processor 44 compares the ratio of power levels within two or more frequency bands to a stored value. In another example, the correlation of changes of power between frequency bands may be compared to a stored value to determine whether to deactivate or continue delivery of PNFS.

If the energy level of the physiological signal is greater than or equal to the threshold value (124), processor 44 deactivates the delivery of PNFS or decreases the intensity of PNFS (108) until the physiological signal indicates therapy delivery is desirable, e.g., the energy level within the selected frequency band is no longer greater than or equal to the threshold value. On the other hand, if the energy level of the physiological signal is not greater than or equal to the threshold value (124), processor 44 may continue delivering PNFS to patient 12 according to the therapy program (110). In some examples, processor 44 generates an efficacy indication and modifies the therapy program if a total count of the efficacy indications exceeds a threshold value, as discussed with respect to FIG. 7.

In the technique shown in FIG. 9, processor 44 may deactivate therapy delivery if the energy level of the physiological signal within one or more frequency bands is greater than or equal to a threshold value. However, in other examples, processor 44 deactivates therapy delivery if the energy level of the physiological signal within one or more frequency bands is greater than a threshold value, less than the threshold value, or less than or equal to the threshold value. In general, in other examples, processor 44 may decrease an intensity of PNFS delivered to region 18 (FIG. 1), rather than deactivating therapy delivery.

As previously described, in some examples, a characteristic of a physiological signal may be associated with a physiological effect of PNFS, which may then be stored as control information to provide closed-loop control of therapy system 10. The particular physiological signal characteristic (as well as the type of physiological parameter) that indicates a particular physiological effect of the PNFS may be determined during a learning stage, such as during a programming session. The programming session may utilize an external trial stimulator for delivery of PNFS if the programming session takes place prior to implantation of IMD 14 within patient 12, or the programming session may utilize IMD 14. In other examples, the characteristic of a physiological signal may be based on a control physiological signal that changes as a function of the physiological parameter of the patient outside of the region 18. Processor 44 may receive the control signal from a sensing module that is separate from IMD 14 or may a sensing module within the same housing as IMD 14 may generate the control physiological signal.

Figure 10:
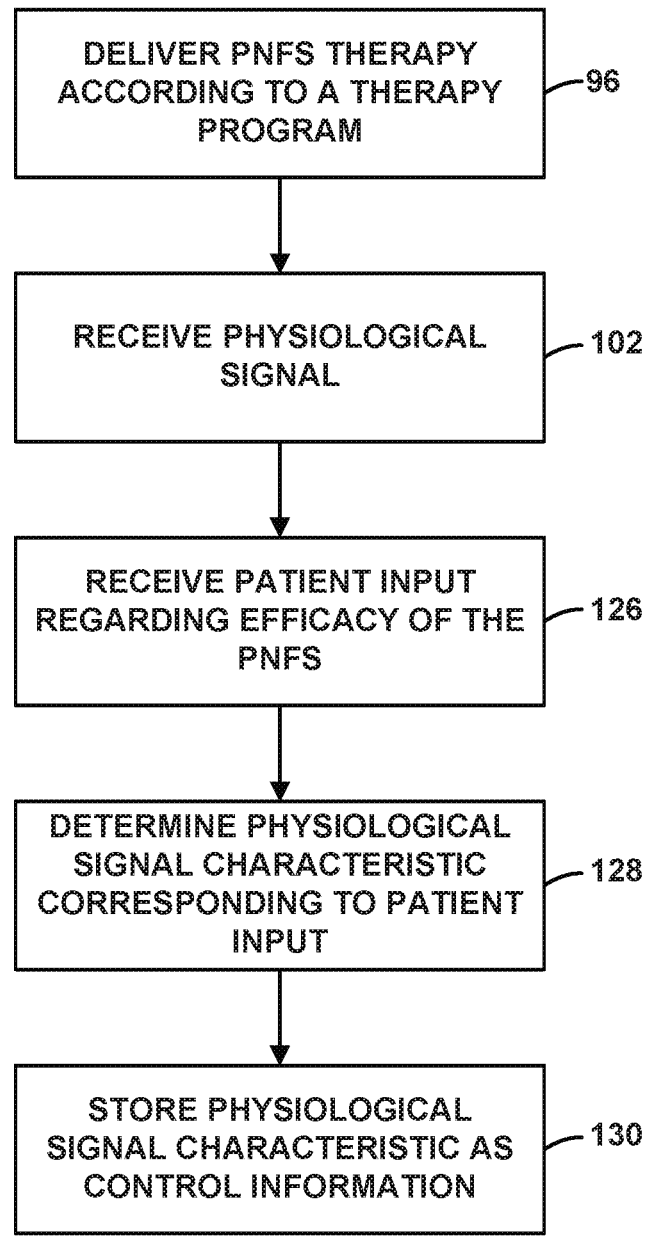
FIG. 10 is a flow diagram illustrating an example technique for determining a physiological signal characteristic that may be used to control PNFS delivery.

FIG. 10 is a flow diagram illustrating an example technique for determining a physiological signal characteristic that indicates a positive patient response to the PNFS. The determined physiological signal characteristic may be stored within memory 46 of IMD 14, memory 62 of clinician programmer 22, memory 82 of patient programmer 28 or a memory of another device. While the description of FIG. 10 primarily refers to processor 60 of clinician programmer 22 (FIG. 3), in other examples, processor 80 of patient programmer 28 (FIG. 4), a processor of another device or more than one processor may perform the technique shown in FIG. 10. Processor 60 controls the delivery of PNFS therapy to patient 12 according to a therapy program (96). The therapy program may have been previously determined to provide efficacious therapy to patient 12. Processor 60 receives a physiological signal (102), e.g., from sensing module 20 or IMD 14. The physiological signal may change as a function of a physiological parameter that reflects an efferent or autonomic response of patient 12 to the PNFS.

Processor 60 receives input from patient 12 or another user regarding the efficacy of the PNFS (126). For example, a user may indicate, via user interface 64 of clinician programmer 22 (FIG. 3) or user interface 84 of patient programmer 28 (FIG. 4), when patient 12 feels therapeutic effects of the PNFS. In response to receiving the input (126), processor 60 determines a characteristic of the physiological signal that corresponds to the patient input (128). The determined physiological signal characteristic may be used in any technique to control PNFS therapy, such as the techniques described above with respect to FIGS. 5-9. In one example, processor 60 determines a peak amplitude, average amplitude or median amplitude of the physiological signal during a time period that temporally correlates to the patient input, such as within a time range of about one second to about 10 minutes prior to and after the patient input was received. However, other time ranges are contemplated. For example, with some physiological signals, such as a respiratory rate or body temperature, a longer period of time (e.g., on the order of minutes) may provide results that are more representative of the patient's current state. The amplitude value may then be stored as the physiological signal characteristic in control information 70 portion of memory 62 (FIG. 3) of clinician programmer 22 or a memory of another device (130).

In another example, processor 60 determines an acceptable window of values for the physiological signal characteristic by determining the peak amplitude value and the lowest amplitude value during a time span of about one second to about 10 minutes prior to and after the patient input was received. Other time ranges are contemplated. The range of amplitude values may then be stored as the physiological signal characteristic in control information 70 portion of memory 62 of clinician programmer 22 or a memory of another device (130).

In another example, processor 60 determines a pattern in the physiological signal waveform that temporally correlates to the patient input, such as within a time range of about one second to about one minute prior to and after the patient input was received, although other time ranges are contemplated. The pattern may then be used as a template that is stored as the physiological signal characteristic in control information 70 portion of memory 62 of clinician programmer 22 or a memory of another device (130).

In another example, processor 60 determines an energy level within one or more frequency bands of the physiological signal waveform that temporally correlates to the patient input, such as within a time range of about one second to about 10 minutes prior to and after the patient input was received. Again, other time ranges are contemplated. The one or more energy levels may then be used to define a template that is stored as the physiological signal characteristic in control information 70 portion of memory 62 of clinician programmer 22 or a memory of another device (130).

In some examples, the patient input may be used during a programming session or chronic therapy delivery to determine the physiological parameter characteristics that provide control information for controlling therapy module 42 of IMD 14 (e.g., to activate or deactivate therapy, or modify a therapy program). Chronic therapy may refer to the period of time during which patient 12 is not in a programming session with the clinician and when IMD 14 is implemented to provide PNFS therapy to patient 12 on a non-temporary basis. Patient 12 may provide input modifying a therapy program until a physiological effect of the PNFS (e.g., a muscle spasm) reached a tolerable (or, in some cases, an intolerable) level. This input may be used to set the lower or upper threshold values of the physiological signal characteristic that acts as the control information in the algorithm that processor 44 of IMD 14 (or another device) implements in order to control therapy module 42 based on a monitored physiological parameter of patient 12.

For example, patient 12 may modify one or more therapy parameter values of the therapy program until the physiological effect of the PNFS mitigates the patient's pain. A first characteristic of the physiological signal that is received when patient 12 indicates the PNFS was effective may be a lower threshold value. Patient 12 may also modify one or more therapy parameter values of the therapy program until the physiological effect of the PNFS exceeds a tolerable level, e.g., the side effects of the PNFS begin to outweigh the therapeutic effects. A second characteristic of the physiological signal that is received when patient 12 indicates the PNFS is no longer tolerable or beneficial may be an upper threshold value. Processor 44 may then control therapy module 42 to maintain the physiological signal received from sensing module 20 at the determined threshold value, or, in some cases, below the threshold value or within the range determined based on the upper and lower threshold values.

As previously described, patient 12 may use patient programmer 28 to make adjustments to therapy programs, thereby resulting in a modified therapy program. The patient's response to therapy delivery according to the modified therapy program may be used to determine whether the modified therapy program is suitable for patient 12. For example, the physiological signal generated by sensing module 20 (FIG. 1) may indicate that the patient's response to delivery of PNFS according to the modified therapy program is undesirable. Control information 54 stored in IMD 14 (FIG. 2A), control information 70 stored in clinician programmer 22 (FIG. 3) or control information 92 stored in patient programmer 28 (FIG. 4) may be used to determine the validity of a modified therapy program.

Figure 11:
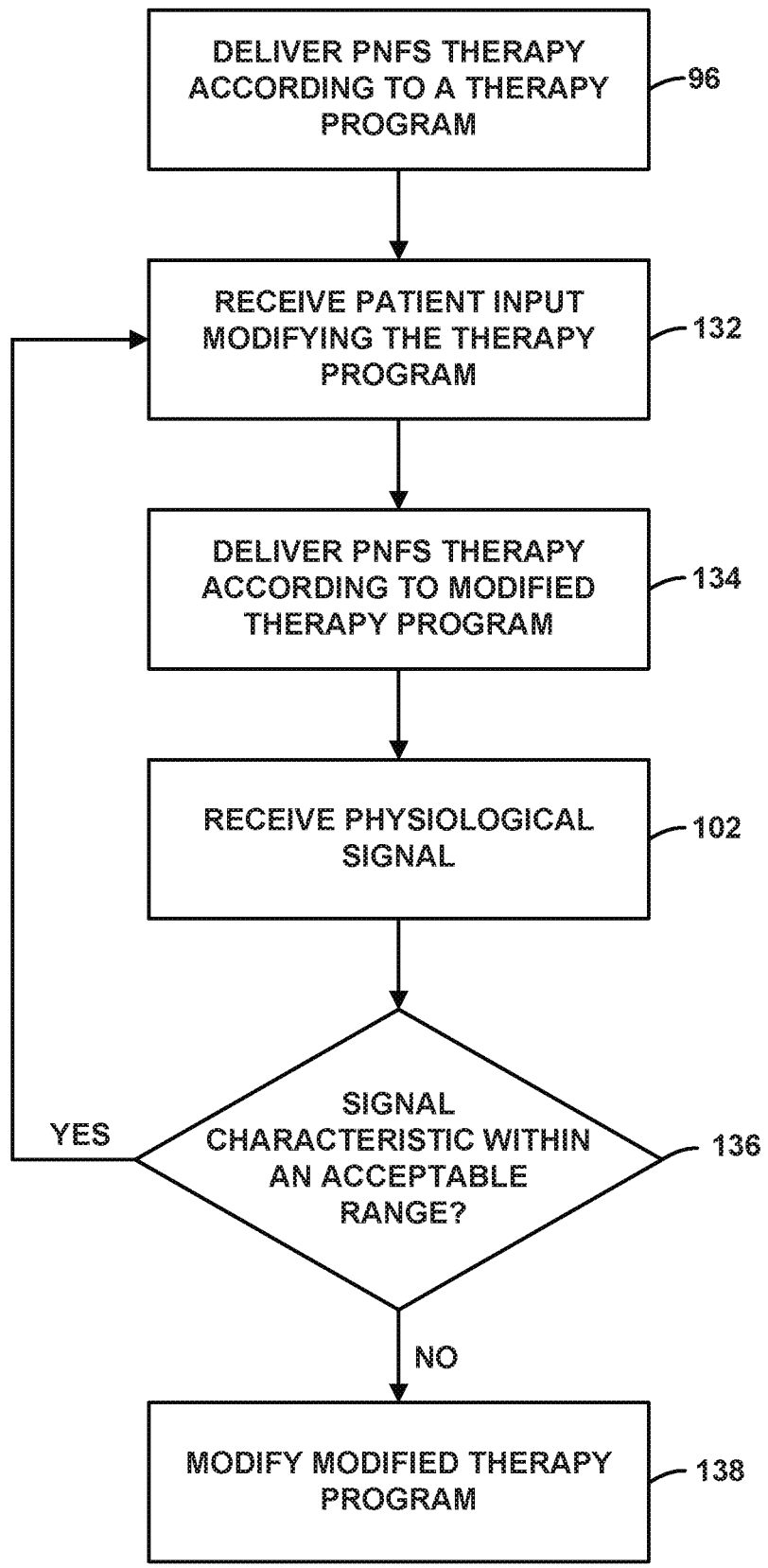
FIG. 11 is a flow diagram illustrating an example technique for determining the validity of a patient's modification to a therapy program.

FIG. 11 is a flow diagram illustrating an example technique for determining the usefulness (or validity) of a patient's modification to a therapy program. Processor 44 of IMD 14 controls therapy module 42 to deliver PNFS to patient 12 according to a therapy program (96). Processor 44 receives patient input regarding a modification to a therapy program (132). In some cases, patient 12 may have the perception that the current therapy program is providing ineffective therapy, and, accordingly, patient 12 may modify the current therapy program. The clinician may program patient programmer 28 to allow patient 12 limited control over therapy delivery. For example, patient programmer 28 may only enable patient 12 to increase or decrease therapy parameter values within a particular range of values that have been determined by the clinician to be beneficial, or at least not harmful, to patient 12. The patient's control over the delivery of PNFS may be useful if patient 12 engages in different activities that result in different levels of pain within region 18 (FIG. 1) of the patient's body. If patient 12 provides input to patient programmer 28 increasing the voltage or current amplitude value of the current therapy program, patient programmer 28 may transmit the patient input to processor 44 of IMD 14 via the respective telemetry modules 86, 50. Patient programmer 28 may, for example, transmit only the therapy parameter values that were modified by patient 12 or programmer 28 may transmit all of the therapy parameter values for the modified therapy program.

Processor 44 of IMD 14 controls therapy module 42 to deliver PNFS to patient 12 according to the modified therapy program (134). Processor 44 may determine the patient's response to the PNFS according to the modified therapy program based on the physiological effects on patient 12. In the technique shown in FIG. 11, processor 44 receives a physiological signal from sensing module 20 (102) and determines whether a characteristic of the physiological signal is within an acceptable range (136). The acceptable range may indicate a range of values that reflect an acceptable physiologic response (e.g., a response that indicates patient 12 is not in pain). In some cases, if the physiological signal characteristic falls outside of the acceptable range, the therapy delivery according to the modified therapy program may be harmful to patient 12. For example, if the physiological signal is an EMG signal indicative of the patient's muscle activity, a high level of muscle activity that falls outside of an acceptable range may indicate that the PNFS is causing muscle spasms, which may be undesirable. The acceptable range of values may be determined, e.g., using the technique described with reference to FIG. 10 or may be preselected by a clinician and stored within IMD 14 and programmers 22, 28.

In one example, processor 44 determines whether the amplitude of the physiological signal is within an acceptable range of amplitude values by comparing the amplitude of the signal to an upper threshold value and a lower threshold value. In the case of an energy level in one or more frequency bands, processor 44 determines whether the energy level is within an acceptable range by comparing the energy level of a frequency band component of the signal to an upper threshold value and a lower threshold value. If the signal characteristic is a pattern in the physiological signal, processor 44 determines whether the pattern is within an acceptable range by comparing the physiological signal waveform to one or more templates.

If the signal characteristic is within an acceptable range (136), processor 44 continues delivering PNFS therapy according to the modified therapy program until patient input is received. In this way, the patient's input modifying a therapy program is regulated based on the physiological effects of the PNFS on patient 12. In some cases, processor 44 may also continue monitoring the physiological signal (102) and may control the delivery of PNFS based on the signal, as described with respect to FIGS. 5-9.

If the signal characteristic is not within an acceptable range (136), processor 44 modifies the modified therapy program (138) in order to generate or select a therapy program that maintains the physiological signal characteristic within an acceptable range. For example, processor 44 may modify the therapy program using any of the techniques described above with respect to FIG. 7, e.g., selecting another stored therapy program or modifying the therapy program using a genetic algorithm or a tree-based structure. Alternatively, processor 44 may revert to the previously-implemented therapy program. Additionally, processor 44 may provide a notification to the patient regarding ineffectiveness of the modified therapy program, e.g., via patient programmer 28.

While the techniques described above with respect to FIGS. 5-11 discuss controlling therapy system 10 based on a detected physiological effect of the PNFS therapy on patient 12, in other examples, therapy system 10 may be controlled based on the detection of a pain state of patient 12. For example, as described below with reference to FIGS. 13 and 14, PNFS may be delivered to patient 12 upon determining a pain state. A pain state refers to a patient state in which the delivery of PNFS to patient 12 may provide relief of pain symptoms felt by patient 12. A characteristic of a physiological signal may be used to characterize a pain state of patient 12.

Figure 12:
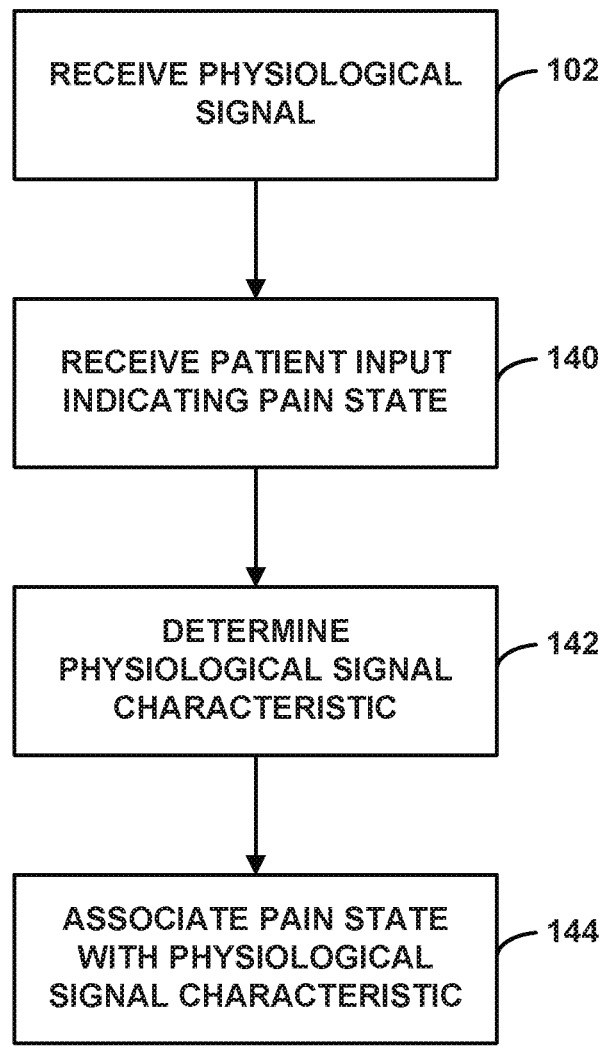
FIG. 12 is a flow diagram illustrating an example technique for associating a patient pain state with a characteristic of a physiological signal.

FIG. 12 is a flow diagram illustrating a technique for associating a patient pain state with a characteristic of a physiological signal. Although the technique shown in FIG. 12 is described as being performed by processor 80 (FIG. 4) of patient programmer 28, in other examples, processor 60 of clinician programmer 22, processor 44 of IMD 14, or a processor of another computing device may associate patient pain states with one or more signal characteristics in accordance with the technique shown in FIG. 12. The technique shown in FIG. 12 may be performed by processor 80 during a learning period, which may be one day to multiple days.

Processor 80 of patient programmer 28 may receive a signal from sensing module 20 indicating activity of a physiological parameter of patient 12, such as the patient's muscle activity or skin conductance (102). When patient 12 feels pain, patient 12 may provide input, e.g., via display 30 or keypad 32 of user interface 84 (FIG. 4). Patient 12 may indicate a pain state using any suitable technique. In one example, patient 12 merely indicates the occurrence of a pain state. For example, user interface 84 of patient programmer 28 may include a button dedicated to recording the time and date of the pain state, and patient 12 may depress the dedicated button. Alternatively, a multifunction button may be used in combination with a particular user interface display to indicate the occurrence of a pain state. In other examples, patient 12 may indicate a type of pain state in addition to indicating the occurrence of a pain state, such as information regarding the severity of the pain state or the location of the pain. For example, patient 12 may select a pain state from a predefined list of pain states (e.g., a list including moderate pain and severe pain), manually input a pain state, select a numerical rating of the severity of the pain state (e.g., a numerical range of 1 through 10, where 10 indicates patient 12 experienced a severe pain state). User interface 84 may present a visual scale, such as the Wong-Baker Faces Pain Rating Scale, and patient 12 may select the relevant pain rating from the visual scale. Other techniques for receiving input regarding a pain state of patient 12 are contemplated.

Upon receiving patient input indicating a pain state (140), processor 80 automatically determines a characteristic of a physiological signal (142). For example, processor 80 may use the technique described with respect to FIG. 10 to determine the characteristic of the physiological signal at the time the patient input was received or within a certain time range including the time at which the patient input was received. Processor 80 associates the physiological signal characteristic with the pain state (144), and stores the information in control information portion 92 of memory 82 (FIG. 4). The control information 92 may be communicated to other devices, such as clinician programmer 22 (FIG. 3), IMD 14 (or IMD 56), or another computing device.

In some cases, upon request by a user, processor 80 may present a list, table or other data format illustrating the pain state (and any relevant pain ratings) and associated physiological signal characteristic via display 30 of patient programmer 28. For example, if the physiological signal characteristic includes a peak or average value of the waveform amplitude of the physiological signal within a certain time range of the patient input, processor 80 may present a list of a plurality of pain states and associated physiological signal amplitude values. The physiological signal characteristics in the list may then be used as a threshold amplitude value for detecting a pain state. As another example, if the physiological signal characteristic includes a trend in the physiological signal waveform within a certain time range of the patient input, processor 80 may present a list of pain states and provide links to a visual representation of the waveform trend. The waveform trend may be used as a template for detecting a pain state based on a physiological signal.

In some cases, the physiological signal characteristic may not provide a direct link to the existence or level of the patient's pain state, and may instead be a surrogate marker that is suggestive of the patient pain state, rather than of pain or another pain-related symptom. Thus, the association between pain states and physiological signal characteristics may be somewhat inaccurate and imprecise. Furthermore, the patient input regarding the pain state may be inaccurate or inconsistent. Accordingly, it may be desirable for the clinician or processor 80 to confirm that a pain state is associated with a particular physiological signal characteristic prior to storing the physiological signal characteristic as control information 92. In some examples, processor 80 or the clinician may record the patient's pain state only after the same or similar physiological signal characteristic is associated with the pain state more than one time. If the physiological signal characteristic is an amplitude value, for example, a similar physiological signal characteristic may be within a particular range, such as about 5% to about 20% of the amplitude value, although other ranges are contemplated.

In some examples, after associating physiological signal characteristics with pain states for one or more patients, a clinician or processor 80 may generate a pain state probability for each physiological signal characteristic. Thus, rather than directly associating a patient pain state with a physiological signal characteristic, processor 80 may assign a probability of the existence or severity of a pain state with the physiological signal characteristic. For example, for a particular physiological signal characteristic, processor 80 may determine that 85% of the time, patient 12 indicated a severe pain state. Programmer 80 may generate a library of physiological signal characteristics and associated pain states or pain state probabilities. The library may be specific to patient 12 (i.e., generated based on information from patient 12) or may be more general, e.g., based on information from more than one patient.

Figure 13:
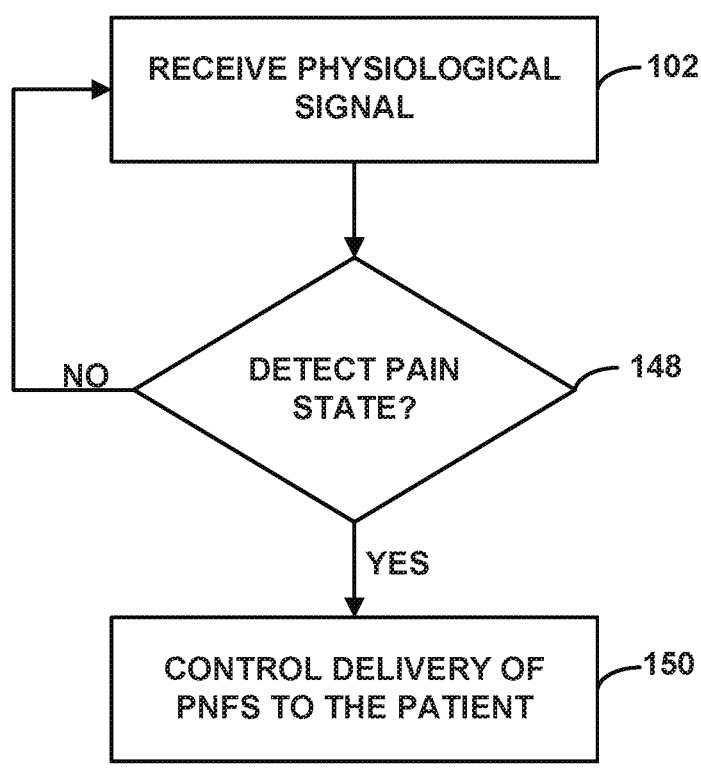
FIGS. 13 and 14 are flow diagrams illustrating example techniques for controlling delivery of PNFS based on a detected pain state.
Figure 14:
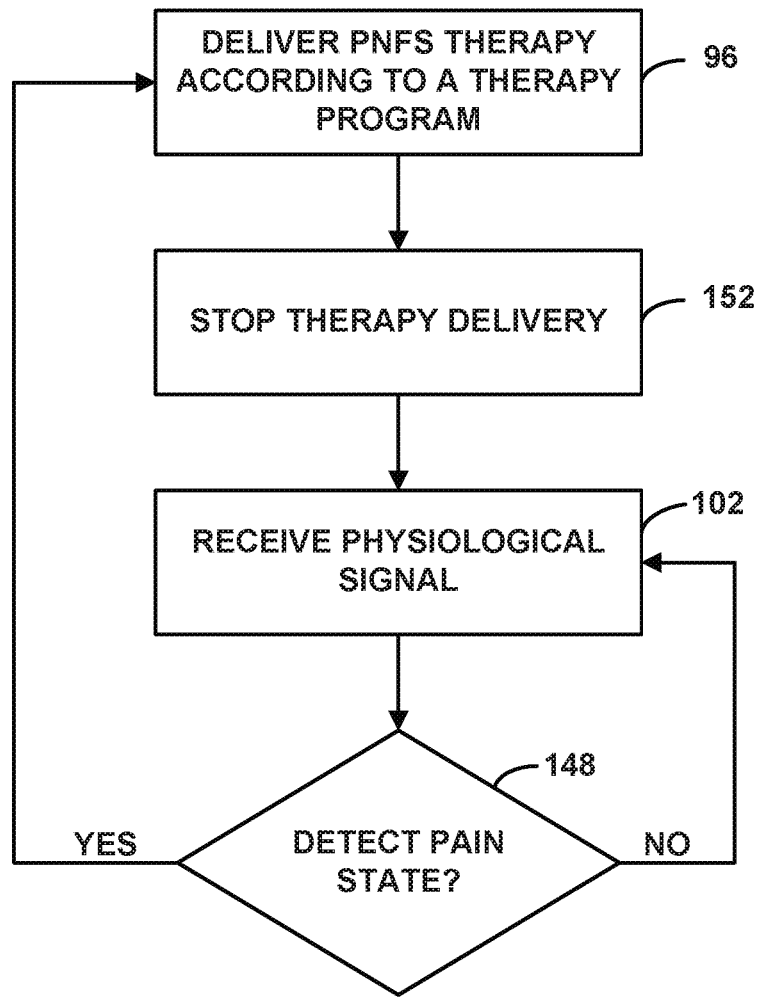

In some examples, the pain state information may be used to control therapy delivery by IMD 14. FIGS. 13 and 14 are flow diagrams illustrating example techniques for controlling therapy delivery based on a detected pain state. If patient 12 suffers from episodic pain, delivering therapy to patient 12 upon detection of a pain state may be an efficient and effective technique for detecting an episode of pain of patient 12 and providing on-demand therapy to patient 12. In the case of both chronic and episodic pain conditions, relief of pain may be maintained for some time after delivery of efficacious PNFS is stopped, thus, although PNFS is not actively delivered to patient 12, patient 12 may experience pain relief. Accordingly, delivering therapy to patient 12 upon detection of a pain state may be an efficient technique for managing chronic pain of patient 12. While processor 44 of IMD 14 is primarily referred to in the description of FIGS. 13 and 14, in other examples, processor 60 of clinician programmer 22, processor 80 of patient programmer 28 or a processor of another device may control PNFS therapy delivery in accordance with the techniques shown in FIGS. 13 and 14.

In the technique shown in FIG. 13, processor 44 monitors a physiological parameter of patient 12 to detect a patient pain state. In particular, processor 44 receives a physiological signal from sensing module 20 (FIG. 1) (102) and determines whether a characteristic of the physiological signal indicates patient 12 is in a pain state (148). For example, processor 44 may compare the amplitude value of the received physiological signal to a threshold value, which may be determined, e.g., using the technique described above with respect to FIG. 12. In other examples, processor 44 may determine whether the characteristic of the physiological signal indicates patient 12 is in a pain state (148) using the template matching and frequency band component analysis techniques similar to those described above with respect to FIGS. 8-9.

If processor 44 detects a pain state (148), processor 44 controls therapy module 42 to initiate therapy delivery or modify a therapy program (150). In some examples, processor 44 selects a therapy program based on the detected pain state. For example, different physiological signal characteristics (e.g., amplitude values or waveform patterns or other morphologies) may be associated with different therapy programs that have been determined by the clinician or processor 44 to provide efficacious therapy to manage the particular pain state of the patient. The clinician or processor 44 may associate the different therapy programs with pain states during a programming session prior to implantation of IMD 14 or after implantation of IMD 14 within patient 12. The pain states, as characterized by a physiological signal characteristic or a range of values of the physiological signal, may be associated with one or more therapy programs in memory 46 of IMD 14, memory 62 of clinician programmer 22 (FIG. 3), memory 82 of patient programmer 28 (FIG. 4) or a memory of another device. In some examples, upon detecting a pain state (148), processor 44 may determine which one or more therapy programs are associated with the pain state and select at least one of the therapy programs to deliver therapy to patient 12.

On the other hand, if processor 44 does not detect a pain state (148), processor 44 continues monitoring the physiological signal until a pain state is detected. In other examples, processor 44 determines a probability of a pain state based on the characteristic of the received physiological signal. If the probability of the pain state associated with the physiological signal characteristic exceeds a threshold level, such as greater than 50% to about 90%, processor 44 controls therapy module 42 to initiate therapy delivery.

The technique shown in FIG. 13 may be implemented to provide closed-loop PNFS therapy to patient 12 as needed, e.g., upon the detection of a pain state. The on-demand therapy may help conserve power source 48 of IMD 14 (FIG. 2A), and helps reduce patient adaptation to the therapy delivery, as discussed above.

As shown in FIG. 14, a patient state that is determined based on a characteristic of a monitored physiological parameter may also be used to deactivate and activate delivery of PNFS to patient 12. In accordance with the technique shown in FIG. 14, processor 44 of IMD 14 delivers PNFS therapy to patient 12 according to a therapy program (96). Processor 44 controls IMD 14 to deliver the PNFS therapy to patient 12 for a predetermined stimulation period, such as about 1 second to about 1 hour. In some examples, the stimulation period may be set by a clinician. Other stimulation periods are contemplated, and may depend upon the type of pain experienced by patient 12.

After the stimulation period, therapy delivery may be deactivated (152), as shown in FIG. 14, or the intensity of the therapy delivery may be decreased. Following the stimulation period, processor 44 may receive a physiological signal from sensing device (102) and determine whether a characteristic of the physiological signal indicates the presence of a pain state (148). If the pain state is detected (148), processor 44 controls therapy module 42 to resume delivering PNFS to region 18 within patient 12. If the pain state is not detected (148), processor 44 continues monitoring the physiological signal without resuming the delivery of PNFS to patient 12 (102). In this way, processor 44 may deliver PNFS to patient 12 while patient 12 is in a pain state and may deactivate or decrease the intensity of stimulation while patient 12 is not in a pain state.

Figure 15A:
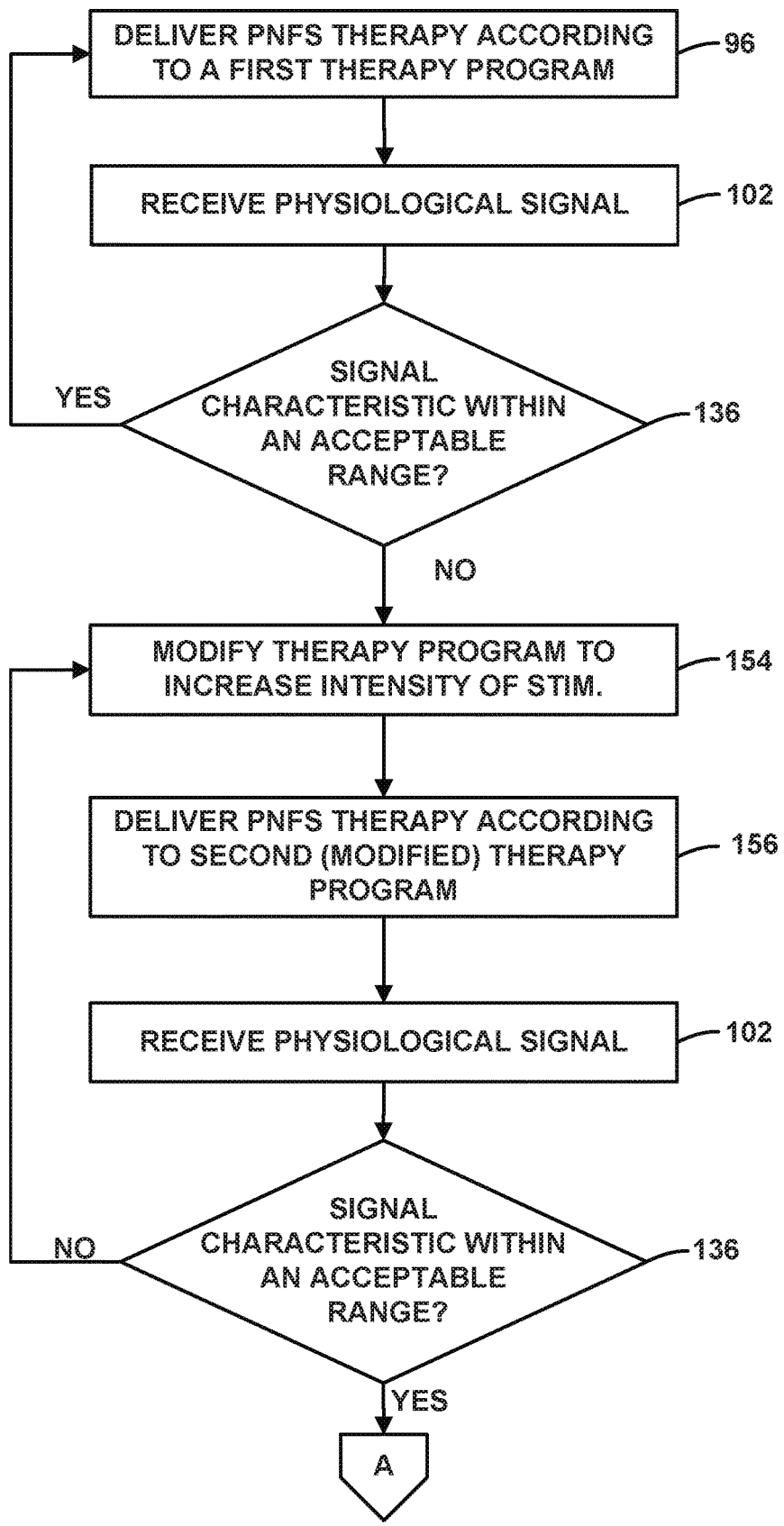
FIGS. 15A and 15B are flow diagrams illustrating an example technique for modifying PNFS.
Figure 15B:
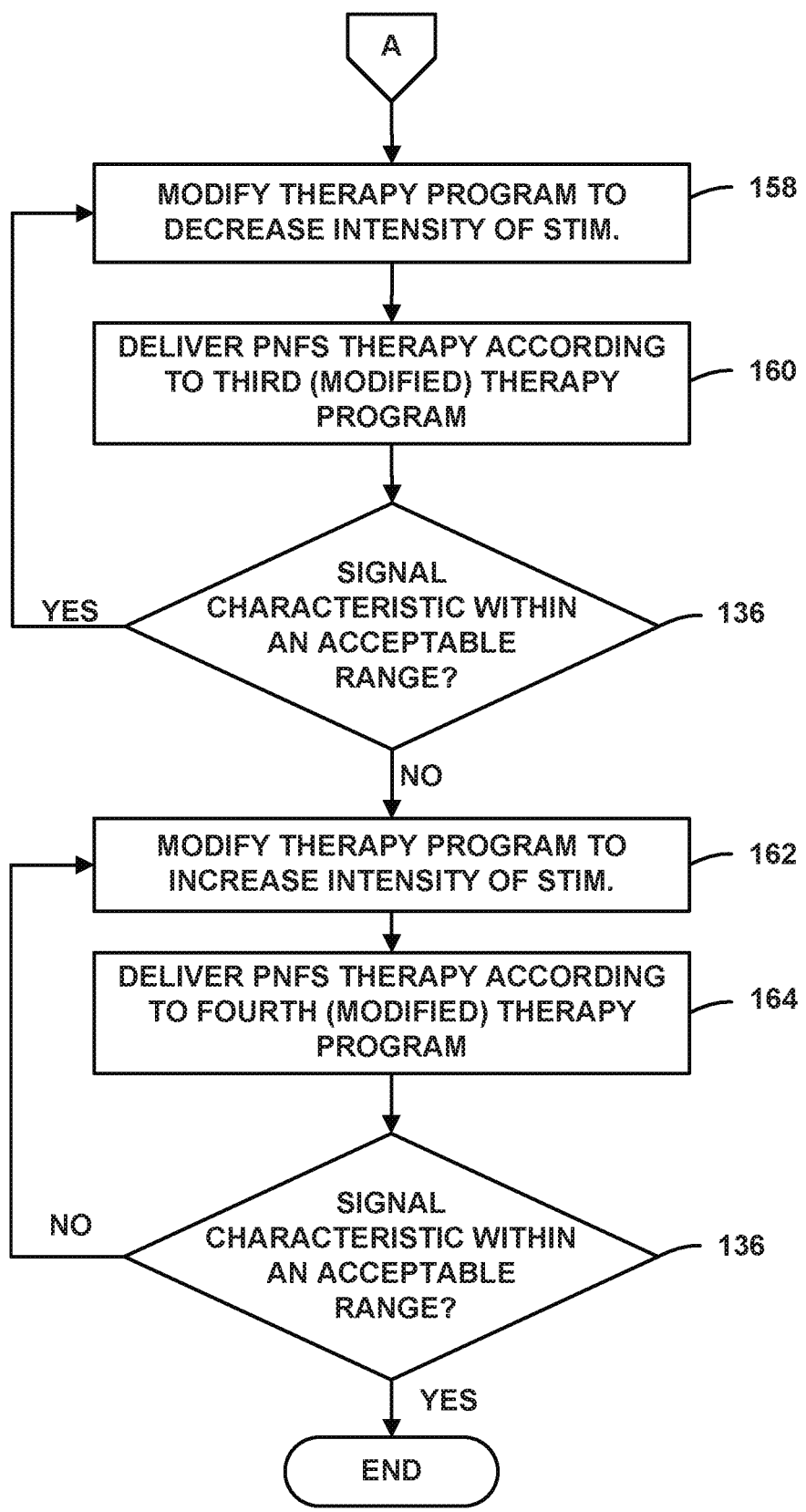

FIGS. 15A and 15B are flow diagrams illustrating an example technique for modifying a therapy program using control information that is based on physiological signals indicative of a patient pain state. The control information may be obtained and associated with a patient pain state or a particular physiological response, e.g., using the technique shown in FIG. 12 and may be stored within IMD 14, clinician programmer 22 or patient programmer 28. While processor 44 of IMD 14 is primarily referred to in the description of FIGS. 15A and 15B, in other examples, processor 60 of clinician programmer 22, processor 80 of patient programmer 28 or a processor of another device may perform any part of the technique shown in FIGS. 15A-15B.

Processor 44 controls therapy module 42 to deliver PNFS to region 18 of patient 12 according to a first therapy program (96). Processor 44 receives a physiological signal from sensing module 20 (102) and determines whether a characteristic of the physiological signal is within an acceptable range (136). As previously described, the acceptable range may indicate the range of values that reflect an acceptable physiologic response (e.g., a response that indicates patient 12 is not in pain). In other examples, processor 44 may determine whether a characteristic of the physiological signal from sensing module 20 substantially matches a control signal, as described with respect to FIGS. 16 and 17. If the physiological signal is within the acceptable range of values (136), processor 44 continues delivering PNFS therapy according to the first therapy program (96). If processor 44 determines that the physiological signal is not within an acceptable range (136), processor 44 determines that modification to the first therapy program is desirable because therapy delivery according to the first therapy program is not efficacious or not sufficiently efficacious. For example, patient 12 may have adapted to the first therapy program over time.

In some cases, processor 44 modifies the first therapy program to increase the intensity of stimulation (154). The intensity of stimulation may be increased by, for example, increasing at least one of the current or voltage amplitude of the first therapy program, the frequency of the first therapy program, and, if the first therapy program defines electrical stimulation pulses, the pulse width of the first therapy program. In addition or instead of modifying the values of the amplitude, frequency or pulse width, processor 44 may modify the electrode configuration that is used to deliver the PNFS, such as by increasing the number of electrodes that are activated in order to yield a larger area of stimulation effect.

Increasing the intensity of stimulation may increase the total energy required by therapy module 42 (FIG. 2A) to generate and deliver the stimulation signals to region 18 (FIG. 1). In some examples, increasing the intensity of stimulation may increase the total volume of the stimulation field generated by delivering the stimulation via electrodes 40 (FIG. 2A). Increasing the total volume of the stimulation field may increase the activation field, which may represent the volume of neural tissue that is activated by the stimulation signals.

After modifying the first therapy program to define a second therapy program including at least one therapy parameter value that differs from the first therapy program (154), processor 44 controls therapy module 42 to deliver PNFS to region 18 according to the second therapy program (156). Processor 44 receives a physiological signal from sensing module 20 (102) and determines whether a characteristic of the physiological signal is within an acceptable range (136). If the physiological signal is not within the acceptable range (136), processor 44 may further increase the intensity of stimulation (154) until the signal is within the acceptable range. If the physiological signal is within the acceptable range (136), processor 44 modifies the second therapy program to decrease the intensity of stimulation (158) and generate a third therapy program. Decreasing the intensity may be useful for, for example, determining whether the intensity may be decreased without decreasing the physiological effect, as indicated by the physiological signal from sensing module 22. Decreasing the intensity of stimulation may help decrease the energy consumption by IMD 14.

The intensity of stimulation may be decreased (158) by modifying the same or a different therapy parameter value as the stimulation parameter modified in order to increase the intensity of stimulation (154). In addition, the intensity of stimulation may be decreased using a different rate than the rate used to increase the intensity (154). That is, in some examples, processor 44 may increase the intensity of stimulation (154) by increasing the value of a stimulation parameter by a first percentage or value, and processor 44 may decrease the intensity of stimulation (158) by decreasing the value of the same stimulation parameter by a second percentage or value that is lower than the first percentage or value.

Processor 44s monitor the physiological effect of the third therapy program on patient 12 by delivering therapy to patient 12 according to the third therapy program (160) and determining whether the physiological signal characteristic is within an acceptable range (136). If the signal characteristic is still within the acceptable range, processor 44 may further decrease the intensity of stimulation (158) until the signal characteristic is outside the acceptable range (136).

After the intensity of stimulation is decreased to a point where the signal characteristic is not within the acceptable range (136), processor 44 may modify the third therapy program to increase the intensity stimulation (162), thereby generating a fourth therapy program. In this iteration of increasing the intensity of stimulation, processor 44 may increase the intensity of stimulation by a smaller factor (e.g., a percentage or incremental parameter value) than the prior modification to increase the stimulation intensity (154).

Processor 44 monitors the physiological effect of the fourth therapy program on patient 12 by delivering therapy to patient 12 according to the fourth therapy program (164) and determining whether the physiological signal characteristic is within an acceptable range (136). If the signal is not within an acceptable range (136), processor 44 continues to increase the intensity of stimulation (162) until the signal characteristic is within the acceptable range. If the signal is within an acceptable range, processor 44 stores the fourth therapy program within memory 46 (within therapy programs 52 section). In some cases, processor 44 may notify another device, such as clinician programmer 22 or patient programmer 28, that the first therapy program was modified, and may transmit information indicative of the therapy parameter values of the fourth therapy program to the other device. In other examples, processor 44 may modify the fourth therapy program to decrease the intensity stimulation. In this iteration of decreasing the intensity of stimulation, processor 44 may decrease the intensity of stimulation by a smaller factor (e.g., a percentage or incremental parameter value) than the prior modification to decrease the stimulation intensity (158).

The technique shown in FIGS. 15A-15B may be used to determine a modification to a therapy program that increases the stimulation intensity and minimizes power usage in order to help conserve power source 48 of IMD 14 (FIG. 2A). By increasing and decreasing the intensity of stimulation by iteratively smaller percentages or parameter values (i.e., in each subsequent therapy program modification step), processor 44 may perform a binary-search type technique to determine at least one therapy parameter value that maintains the physiological effects of stimulation on patient 12 within a particular range, while minimizing the energy required by TMD 14 to generate and deliver the efficacious stimulation therapy to patient 12.

Processor 44 may make any suitable number of iterations to decrease and increase the intensity of stimulation. For example, in other examples, after the signal characteristic is within the acceptable range (136) following therapy delivery according to the third therapy program (160), processor 44 may store the third therapy program within memory 46 (within therapy programs 52 section) rather than modifying the third therapy program to increase the intensity of stimulation. As another example, in other examples, after the signal characteristic is within the acceptable range (136) following therapy delivery according to the fourth therapy program (162), processor 44 may modify the fourth therapy program to decrease the intensity of stimulation.

Rather than controlling therapy module 42 of IMD 14 based on a stored physiological characteristic (e.g., determined using the technique shown in FIG. 10), in other examples, processor 44 may control therapy module 42 based on a received control physiological signal. The control physiological signal may be generated by a sensing module within IMD 14, by sensing module 20 (FIG. 1) or a separate sensing module. FIG. 16 is a conceptual diagram of therapy system 170 that includes sensing module 172 that is separate from IMD 14 and sensing module 20. Therapy system 170 is substantially similar to therapy system 10 of FIG. 1 and may include IMD 14 coupled to lead 16 to deliver PNFS to region 18 of the patient's body in which patient 12 perceives pain. Although not shown in FIG. 16, therapy system 170 may include clinician programmer 22 and/or patient programmer 28, which may each be configured to communicate with sensing module 172.

Sensing module 172 may generate a control physiological signal that indicates an activity of a physiological parameter of patient 12 at a "normal" level, e.g., generally unaffected by the patient's pain or the delivery of PNFS. For example, if patient 12 experiences back spasms within region 18, sensing module 172 may be positioned to generate a control signal that reflects the physiological parameter activity within an area of the patient's body that does not experience back spasms (e.g., another region within the back, which may reflect a baseline (normal) level of muscle activity). The control signal may indicate, for example, muscle activity (e.g., EMG), skin temperature, blood flow, and the like. Accordingly, in some examples, sensing module 172 may generate a control physiological signal that indicates activity of a physiological parameter of patient 12 outside of the region 18 to which IMD 14 delivers PNFS. For example, sensing module 172 may be implanted within patient 12 outside of region 18 (e.g., about 2 centimeters (cm) to 20 cm or greater from region) or may be external to patient 12 outside of region 18, which includes the region of the patient's epidermis that substantially corresponds to region 18. The signal from sensing module 172 may be used to determine a physiological signal characteristic that does not result from the delivery of PNFS.

Sensing module 172 may transmit the control physiological signal to IMD 14. The control signal may be sent substantially in real time, e.g., indicating the current activity of the physiological parameter, such as within the previous 1 ms to about 1 second, although other time ranges or contemplated. In other examples, sensing module 172 may periodically transmit a control signal to IMD 14 that does not indicate the most recent activity of the physiological parameter, but may still generally indicate a baseline state for the physiological signal generated by sensing module 20, which indicates the physiological effects of the PNFS.

In examples in which IMD 14 includes a sensing module that generates the control physiological signal, IMD 14 may sense the physiological parameter outside of region 18 with electrodes that are coupled to lead 16, which may include the same electrode array 40 as the array used to deliver PNFS. Depending on the relative size of region 18 compared to the electrode array 40, electrode array 40 may include electrodes that are both within region 18 to deliver PNFS to region and outside of region 18 to sense a physiological parameter. In examples in which sensing module 20 (FIG. 1) is used to generate the control physiological signal, sensing module 20 may also include electrodes that are within region 18 and outside of region 18. For example, one subset of electrodes of sensing module 20 may be used to detect the physiological signal that indicates the physiological effects of PNFS and another subset of electrodes may be used to detect a control signal. The first and second subsets of electrodes may be spaced from each other such that sensing module 20 is capable of sensing the physiological parameter of patient 12 in different areas of the patient's body to distinguish between the physiological effects of the PNFS and the normal physiological parameter levels (e.g., generally not reflecting the physiological effects of the PNFS).

Figure 17:
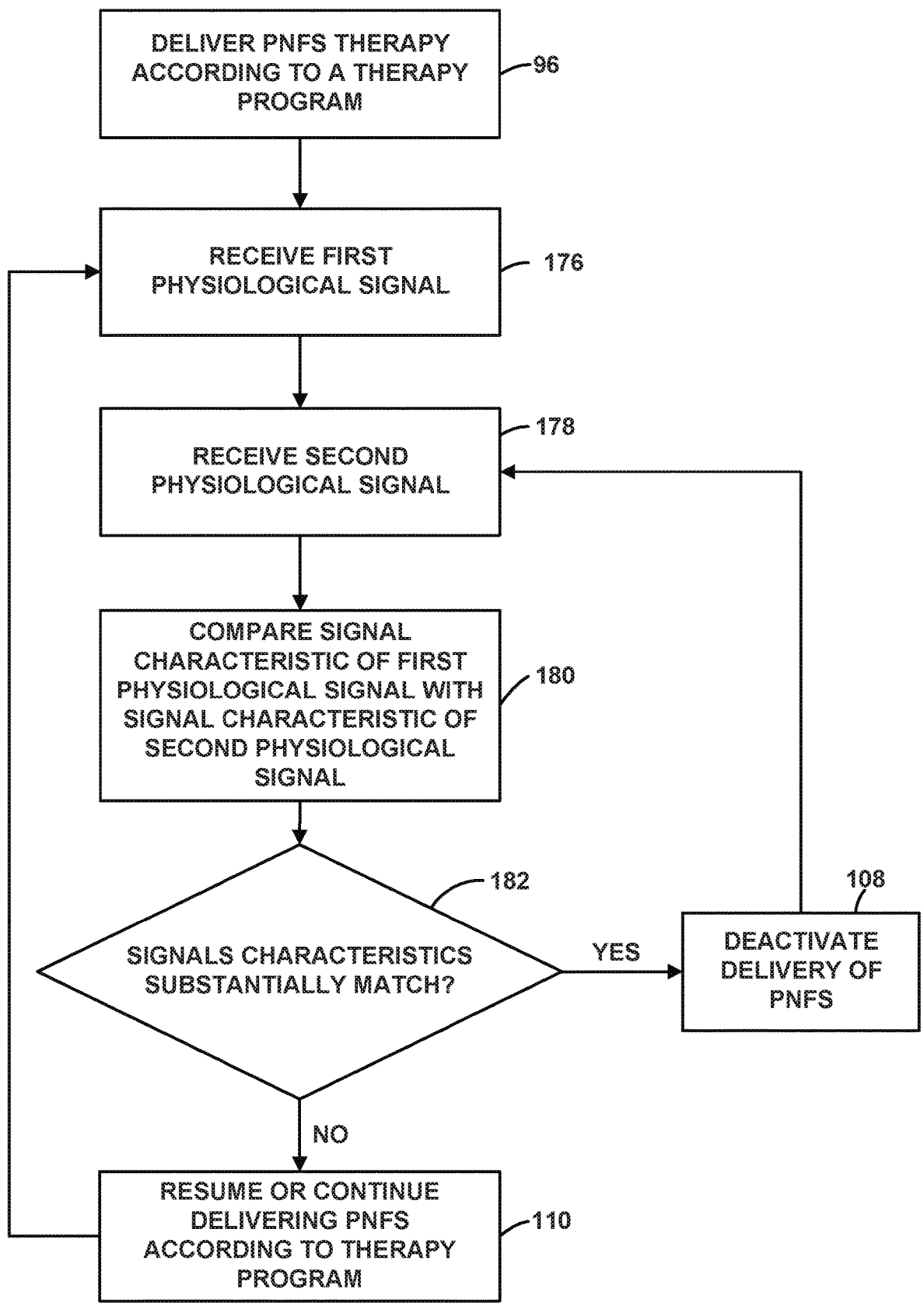
FIG. 17 is a flow diagram illustrating an example technique for controlling an implantable medical device based on a control physiological signal.

FIG. 17 is a flow diagram illustrating an example technique for controlling an implantable medical device based on a sensed physiological parameter of the patient. While processor 44 of IMD 14 is primarily referred to in the description of FIG. 17, in other examples, processor 60 of clinician programmer 22, processor 80 of patient programmer, or a processor of another device may control therapy module 42 based on a control physiological signal generated by sensing module 172.

Therapy module 42 of IMD 14 delivers PNFS to patient 12 according to a therapy program (96). As previously described, processor 44 of IMD 14 may control therapy module 42 to deliver the PNFS. Processor 44 receives a first physiological signal from sensing module 20, which indicates a physiological effect of the PNFS or physiological parameter activity that indicates the patient's pain (176). Processor 44 also receives a second, control physiological signal from sensing module 172 (178), which indicates the physiological parameter activity of the patient that is generally unaffected by the delivery of PNFS. For example, the second physiological signal may be generated within an area outside of region 18 (FIG. 1) of the patient's body in which PNFS is delivered. Many physiological effects from PNFS may be relatively local in nature (e.g., skin temperature, sweating, EMG, and the like), and, accordingly, the second physiological signal characteristic may be distanced from region 18 (FIG. 1) a relatively small distance (e.g., about 2 cm to about 20 cm or greater).

Processor 44 compares the first physiological signal to the second physiological signal (180). In the example shown in FIG. 17, processor 44 may determine a first characteristic of the first physiological signal, such as a peak, average or median amplitude within a sample time window, a frequency characteristic (e.g., a power level within a selected frequency band or a ratio of powers), a pattern in the first physiological signal waveform over time, and so forth. Processor 44 may also determine a second characteristic of the second physiological signal, where the type of second characteristic is similar to the first characteristic (e.g., both may be amplitude values or patterns of the waveforms). Processor 44 may then compare the first and second characteristics (180).

If the first and second signal characteristics substantially match (182), processor 44 determines that the PNFS has been effective, and processor 44 controls therapy module 42 to deactivate the delivery of PNFS to region 18 (108). Alternatively, processor 44 may merely decrease the intensity of the PNFS delivered to region. If the first and second signal characteristics do not substantially match (182), processor 44 may determine that the PNFS has not been effective, and processor may control therapy module 42 of IMD 14 to resume or continue delivering PNFS to the patient according to the therapy program (110).

In other examples, processor 44 may modify the therapy program if the first characteristic of the first physiological signal from sensing module 22 does not substantially match the corresponding characteristic of the second, control signal from sensing module 172. For example, similar to the technique shown in FIG. 7, processor 44 may determine efficacy indications based on the comparison between the first physiological signal from sensing module 22 and the second, control signal from sensing module 172. If the number of efficacy indications exceeds a threshold, processor 44 may determine that the current therapy program is ineffective and may modify the current therapy program, such as by selecting a different therapy program or modifying one or more stimulation parameter values of the current therapy program.

Various examples have been described in this disclosure. These and other examples are within the scope of the following claims. For example, while PNFS is primarily described herein, the techniques for controlling therapy delivery described herein may also be applicable to other types of therapy, such as peripheral nerve stimulation (PNS). In addition, therapy system 10 may deliver PNFS to patient 12 in combination with one or more other therapies, as described in U.S. patent application Ser. No. 11/450,133 to Rooney et al., which was previously incorporated by reference. Examples of other therapies include spinal cord stimulation or delivery of a therapeutic agent, anti-inflammatory agents such as steroids, NSAIDS, TNF-alpha inhibitors (soluble receptors, antibodies, etc.), local anesthetics, and NMDA antagonists (ketamine, etc.).

In addition, in other examples, PNFS may be delivered by an IMD including electrodes on one or more surfaces of the IMD housing, as described in commonly-assigned U.S. patent application Ser. No. 11/450,127 to Rooney et al., entitled, "IMPLANTABLE MEDICAL DEVICE WITH ELECTRODES ON MULTIPLE HOUSINGS SURFACES," which was filed on Jun. 9, 2006 and is incorporated herein by reference in its entirety. Examples of therapeutic agents for relieving pain are also described in commonly-assigned U.S. patent application Ser. No. 11/374,852 to Heruth et al., entitled, "REGIONAL THERAPIES FOR TREATMENT OF PAIN," which was filed on Mar. 14, 2006 and is incorporated herein by reference in its entirety.

The techniques described in this disclosure, including those attributed to IMD 14, clinician programmer 22, patient programmer 28, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 44 of IMD 14, processor 60 of clinician programmer 22, and/or processor 80 of clinician programmer 28, any one or more parts of the techniques described herein may be implemented by a processor of one of IMD 14, clinician programmer 22, patient programmer 28, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the disclosure have been described. These and other examples are within the scope of the following example statements.

The invention claimed is:

1. A method comprising:
   delivering peripheral nerve field stimulation to a region of a body of a patient in which the patient experiences pain via at least one electrode implanted in the region;
   receiving a signal indicative of a physiological parameter of the patient;
   determining the patient pain state based on the signal; and
   based on the patient pain state, controlling the delivery of peripheral nerve field stimulation to a region of a body of the patient in which the patient experiences pain via at least one electrode implanted in the region, wherein controlling the delivery of the peripheral nerve field stimulation comprises deactivating the delivery of the peripheral nerve field stimulation to the region of the body and wherein the peripheral nerve field stimulation is not deliberately targeting a specific nerve.

2. The method of claim 1, wherein the patient pain state is a first patient pain state, and wherein the method further comprises:
   determining a second patient pain state based on the signal; and
   based on the second patient pain state, controlling the delivery of the peripheral nerve field stimulation comprising initiating the delivery of the peripheral nerve field stimulation.

3. The method of claim 1, wherein delivering peripheral nerve field stimulation to the region of the body of the patient in which the patient experiences pain occurs prior to determining the patient pain state.

4. The method of claim 1, wherein the patient pain state is a first patient pain state, and wherein the method further comprises:
   prior to determining a second patient pain state, delivering peripheral nerve field stimulation to the region of the body of the patient in which the patient experiences pain via the at least one electrode implanted in the region,
   determining the second patient pain state based on the signal; and
   based on the second patient pain state, controlling the delivery of the peripheral nerve field stimulation comprising continuing the delivery of the peripheral nerve field stimulation.

5. The method of claim 1, wherein the patient pain state is a first patient pain state, and wherein the method further comprises:

determining a second patient pain state based on the signal; and based on the second patient pain state, controlling the delivery of the peripheral nerve field stimulation comprising modifying a therapy program based on the patient pain state.

6. The method of claim 1, wherein the patient pain state is a first patient pain state, and wherein the method further comprises:

determining a second patient pain state based on the signal; and based on the second patient pain state, controlling the delivery of the peripheral nerve field stimulation comprising selecting a therapy program based on the patient pain state.

7. The method of claim 1, further comprising:

receiving patient input indicating the patient pain state; and associating the patient pain state with a characteristic of the signal, wherein controlling the delivery of the peripheral nerve field stimulation comprises detecting the characteristic of the signal.

8. The method of claim 1, wherein determining the patient pain state comprises at least one of comparing a peak amplitude of the signal to a threshold amplitude, comparing an average amplitude of the signal to the threshold amplitude, comparing a median amplitude of the signal to the threshold amplitude, comparing a trend in a waveform of the signal over time to a template, comparing a power level within one or more frequency bands of the signal to a threshold power level or comparing a ratio of power levels in two or more frequency bands of the signal to a threshold power level ratio.

9. The method of claim 1, wherein the physiological parameter comprises at least one of a heart rate, respiratory rate, electrodermal activity, muscle activity, blood flow rate, sweat gland activity, pilomotor reflex or thermal activity of the patient.

10. A system comprising:

a sensing circuitry configured to generate a signal indicative of a physiological parameter of a patient;

a medical device configured to deliver peripheral nerve field stimulation to a region of a body of the patient in which the patient experiences pain via at least one electrode implanted in the region, wherein the peripheral nerve field stimulation does not deliberately target a specific nerve; and a processor configured to receive the signal from the sensing circuitry, determine a patient pain state based on the signal, and control the medical device to deliver the peripheral nerve field stimulation to the patient based on the patient pain state, wherein the processor is configured to control the medical device based on the patient pain state by at least deactivating the delivery of the peripheral nerve field stimulation to the region of the body based on the patient pain state.

11. The system of claim 10, wherein the sensing circuitry is configured to generate a signal indicative of at least one of a heart rate, respiratory rate, electrodermal activity, muscle activity, blood flow rate, sweat gland activity, pilomotor reflex or thermal activity of the patient.

12. The system of claim 10, wherein the patient pain state is a first patient pain state, and wherein the processor is further configured to:

determine a second patient pain state based on the signal; and control the medical device based on the second patient pain state by at least initiating the delivery of the peripheral nerve field stimulation.

13. The system of claim 10, wherein the medical device is configured to deliver peripheral nerve field stimulation to the region of the body of the patient during a stimulation period, and wherein the processor is configured to determine the patient pain state after the stimulation period.

14. The system of claim 10, wherein the patient pain state is a first patient pain state, and wherein the processor is further configured to:

determine a second patient pain state based on the signal; and control the medical device based on the second patient pain state by at least modifying a therapy program.

15. The system of claim 10, further comprising a memory that stores a plurality of therapy programs and information associating at least two of the therapy programs with different patient pain states, wherein the patient pain state is a first patient pain state, and wherein the processor is further configured to:

determine a second patient pain state based on the signal; and control the medical device based on the second patient pain state by at least selecting at least one therapy program of the plurality of therapy programs stored in the memory.

16. The system of claim 10, wherein the processor is configured to receive patient input indicating the patient pain state and associates the patient pain state with a characteristic of the signal.

17. The system of claim 10, wherein the processor is configured to determine the patient pain state by at least one of comparing a peak amplitude of the signal to a threshold amplitude, comparing an average amplitude of the signal to the threshold amplitude, comparing a median amplitude of the signal to the threshold amplitude, comparing a trend in a waveform of the signal over time to a template, comparing a power level within one or more frequency bands of the signal to a threshold power level or comparing a ratio of power levels in two or more frequency bands of the signal to a threshold power level ratio.

18. A system comprising:

means for delivering peripheral nerve field stimulation to a region of a body of a patient in which the patient experiences pain via at least one electrode implanted in the region;

means for receiving a signal indicative of a physiological parameter of the patient;

means for determining the patient pain state based on the signal; and means for controlling the means for delivering peripheral nerve field stimulation by at least controlling the means for delivering peripheral nerve field stimulation to deactivate the delivery of the peripheral nerve field stimulation to the region of the body, wherein the peripheral nerve field stimulation is not deliberately targeting a specific nerve.

19. The system of claim 18, further comprising means for receiving patient input indicating the patient pain state and means for associating the patient pain state with a characteristic of the signal, wherein the means for controlling the means for delivering peripheral nerve field stimulation comprises means for detecting the characteristic of the signal.

* * * * *